(12) United States Patent
Panther

(10) Patent No.: US 10,187,918 B2
(45) Date of Patent: Jan. 22, 2019

(54) SECURE PAIRING OF DEVICES VIA PAIRING FACILITATOR-INTERMEDIARY DEVICE

(71) Applicant: Fitbit, Inc., San Francisco, CA (US)

(72) Inventor: Heiko Gernot Albert Panther, Oakland, CA (US)

(73) Assignee: Fitbit, Inc., San Francisco, CA (US)

( * ) Notice: Subject to any disclaimer, the term of this patent is extended or adjusted under 35 U.S.C. 154(b) by 0 days.

(21) Appl. No.: 15/682,494

(22) Filed: Aug. 21, 2017

(65) Prior Publication Data
US 2018/0035481 A1    Feb. 1, 2018

Related U.S. Application Data

(63) Continuation of application No. 15/012,552, filed on Feb. 1, 2016, now Pat. No. 9,743,443, which is a
(Continued)

(51) Int. Cl.
*H04W 76/14* (2018.01)
*A61B 5/00* (2006.01)
(Continued)

(52) U.S. Cl.
CPC ........... *H04W 76/14* (2018.02); *A61B 5/0024* (2013.01); *A61B 5/681* (2013.01);
(Continued)

(58) Field of Classification Search
CPC ..... H04W 76/14; H04W 12/00; H04W 12/02; A61B 5/0024; A61B 5/681; A61B 5/6824;
(Continued)

(56) References Cited

U.S. PATENT DOCUMENTS

| 2,717,736 A | 9/1955 | Schlesinger |
| 2,827,309 A | 3/1958 | Fred |

(Continued)

FOREIGN PATENT DOCUMENTS

| JP | 11-347021 | 12/1999 |
| RU | 2178588 | 1/2002 |

(Continued)

OTHER PUBLICATIONS

Chandrasekar et al., Plug-and-Play, Single-Chip Photoplethysmography, 34th Annual International Conference of the IEEE EMBS, San Diego, California USA, Aug. 28-Sep. 1, 2012, 4 pages.
(Continued)

*Primary Examiner* — Darren B Schwartz
(74) *Attorney, Agent, or Firm* — Knobbe, Martens, Olson & Bear, LLP

(57) ABSTRACT

The present inventions, in one aspect, are directed to systems and circuitry for and/or methods of establishing communication having one or more pairing facilitator-intermediary devices (for example, a network connected server) to enable or facilitate pairing and/or registering at least two devices (e.g., (i) a portable biometric monitoring device and (ii) a smartphone, laptop and/or tablet) to, for example, recognize, interact and/or enable interoperability between such devices. The pairing facilitator-intermediary device may responsively communicates information to one or more of the devices (to be paired or registered) which, in response, enable or facilitate such devices to pair or register. The present inventions may be advantageous where one or both of the devices to be paired or registered is/are not configured (e.g., include a user interface or certain communication circuitry that is configured or includes functionality) to pair devices without use of a facilitator-intermediary device.

17 Claims, 18 Drawing Sheets

Related U.S. Application Data continuation of application No. 14/642,352, filed on Mar. 9, 2015, now Pat. No. 9,253,168, which is a continuation of application No. 13/872,015, filed on Apr. 26, 2013, now abandoned.

(60) Provisional application No. 61/638,650, filed on Apr. 26, 2012.

(51) Int. Cl.

| | |
|---|---|
| *H04W 12/00* | (2009.01) |
| *H04W 12/02* | (2009.01) |
| *H04L 29/06* | (2006.01) |
| *A61B 5/0205* | (2006.01) |
| *A61B 5/11* | (2006.01) |

(52) U.S. Cl.
CPC ...... *H04L 63/0464* (2013.01); *H04L 63/0471* (2013.01); *H04W 12/00* (2013.01); *H04W 12/02* (2013.01); *A61B 5/0205* (2013.01); *A61B 5/11* (2013.01); *A61B 5/6824* (2013.01); *A61B 5/6829* (2013.01); *H04L 63/0281* (2013.01)

(58) Field of Classification Search
CPC ....... A61B 5/0205; A61B 5/11; A61B 5/6829; H04L 63/0471; H04L 63/0464; H04L 63/0281
See application file for complete search history.

(56) References Cited

U.S. PATENT DOCUMENTS

| | | |
|---|---|---|
| 2,883,255 A | 4/1959 | Anderson |
| 3,163,856 A | 12/1964 | Kirby |
| 3,250,270 A | 5/1966 | Lyon |
| 3,522,383 A | 7/1970 | Chang |
| 3,918,658 A | 11/1975 | Beller |
| 4,192,000 A | 3/1980 | Lipsey |
| 4,244,020 A | 1/1981 | Ratcliff |
| 4,281,663 A | 8/1981 | Pringle |
| 4,284,849 A | 8/1981 | Anderson et al. |
| 4,312,358 A | 1/1982 | Barney |
| 4,367,752 A | 1/1983 | Jimenez et al. |
| 4,390,922 A | 6/1983 | Pelliccia |
| 4,407,295 A | 10/1983 | Steuer et al. |
| 4,425,921 A | 1/1984 | Fujisaki et al. |
| 4,575,804 A | 3/1986 | Ratcliff |
| 4,578,769 A | 3/1986 | Frederick |
| 4,617,525 A | 10/1986 | Lloyd |
| 4,887,249 A | 12/1989 | Thinesen |
| 4,930,518 A | 6/1990 | Hrushesky |
| 4,977,509 A | 12/1990 | Pitchford et al. |
| 5,058,427 A | 10/1991 | Brandt |
| 5,224,059 A | 6/1993 | Nitta et al. |
| 5,295,085 A | 3/1994 | Hoffacker |
| 5,314,389 A | 5/1994 | Dotan |
| 5,323,650 A | 6/1994 | Fullen et al. |
| 5,365,930 A | 11/1994 | Takashima et al. |
| 5,446,705 A | 8/1995 | Haas et al. |
| 5,456,648 A | 10/1995 | Edinburg et al. |
| 5,553,296 A | 9/1996 | Forrest et al. |
| 5,583,776 A | 12/1996 | Levi et al. |
| 5,645,509 A | 7/1997 | Brewer et al. |
| 5,671,162 A | 9/1997 | Werbin |
| 5,704,350 A | 1/1998 | Williams, III |
| 5,724,265 A | 3/1998 | Hutchings |
| 5,817,008 A | 10/1998 | Rafert et al. |
| 5,890,128 A | 3/1999 | Diaz et al. |
| 5,891,042 A | 4/1999 | Sham et al. |
| 5,894,454 A | 4/1999 | Kondo |
| 5,899,963 A | 5/1999 | Hutchings |
| 5,941,828 A | 8/1999 | Archibald et al. |
| 5,947,868 A | 9/1999 | Dugan |
| 5,955,667 A | 9/1999 | Fyfe |
| 5,976,083 A | 11/1999 | Richardson et al. |
| 6,018,705 A | 1/2000 | Gaudet et al. |
| 6,077,193 A | 6/2000 | Buhler et al. |
| 6,078,874 A | 6/2000 | Piety et al. |
| 6,085,248 A | 7/2000 | Sambamurthy et al. |
| 6,129,686 A | 10/2000 | Friedman |
| 6,145,389 A | 11/2000 | Ebeling et al. |
| 6,183,425 B1 | 2/2001 | Whalen et al. |
| 6,213,872 B1 | 4/2001 | Harada et al. |
| 6,241,684 B1 | 6/2001 | Amana et al. |
| 6,287,262 B1 | 9/2001 | Amana et al. |
| 6,301,964 B1 | 10/2001 | Fyfe et al. |
| 6,302,789 B2 | 10/2001 | Harada et al. |
| 6,305,221 B1 | 10/2001 | Hutchings |
| 6,309,360 B1 | 10/2001 | Mault |
| 6,469,639 B2 | 10/2002 | Tanenhaus et al. |
| 6,478,736 B1 | 11/2002 | Mault |
| 6,513,381 B2 | 2/2003 | Fyfe et al. |
| 6,513,532 B2 | 2/2003 | Mault et al. |
| 6,527,711 B1 | 3/2003 | Stivoric et al. |
| 6,529,827 B1 | 3/2003 | Beason et al. |
| 6,561,951 B2 | 5/2003 | Cannon et al. |
| 6,571,200 B1 | 5/2003 | Mault |
| 6,585,622 B1 | 7/2003 | Shum et al. |
| 6,607,493 B2 | 8/2003 | Song |
| 6,620,078 B2 | 9/2003 | Pfeffer |
| 6,678,629 B2 | 1/2004 | Tsuji |
| 6,699,188 B2 | 3/2004 | Wessel |
| 6,761,064 B2 | 7/2004 | Tsuji |
| 6,772,331 B1 | 8/2004 | Hind |
| 6,790,178 B1 | 9/2004 | Mault et al. |
| 6,808,473 B2 | 10/2004 | Hisano et al. |
| 6,811,516 B1 | 11/2004 | Dugan |
| 6,813,582 B2 | 11/2004 | Levi et al. |
| 6,813,931 B2 | 11/2004 | Yadav et al. |
| 6,856,938 B2 | 2/2005 | Kurtz |
| 6,862,575 B1 | 3/2005 | Anttila et al. |
| 7,041,032 B1 | 5/2006 | Calvano |
| 7,062,225 B2 | 6/2006 | White |
| 7,099,237 B2 | 8/2006 | Lall |
| 7,133,690 B2 | 11/2006 | Ranta-Aho et al. |
| 7,162,368 B2 | 1/2007 | Levi et al. |
| 7,171,331 B2 | 1/2007 | Vock et al. |
| 7,200,517 B2 | 4/2007 | Darley et al. |
| 7,246,033 B1 | 7/2007 | Kudo |
| 7,261,690 B2 | 8/2007 | Teller et al. |
| 7,272,982 B2 | 9/2007 | Neuhauser et al. |
| 7,285,090 B2 | 10/2007 | Stivoric et al. |
| 7,373,820 B1 | 5/2008 | James |
| 7,443,292 B2 | 10/2008 | Jensen et al. |
| 7,457,724 B2 | 11/2008 | Vock et al. |
| 7,467,060 B2 | 12/2008 | Kulach et al. |
| 7,502,643 B2 | 3/2009 | Farringdon et al. |
| 7,505,865 B2 | 3/2009 | Ohkubo et al. |
| 7,539,532 B2 | 5/2009 | Tran |
| 7,558,622 B2 | 7/2009 | Tran |
| 7,559,877 B2 | 7/2009 | Parks et al. |
| 7,608,050 B2 | 10/2009 | Shuqq |
| 7,653,508 B1 | 1/2010 | Kahn et al. |
| 7,690,556 B1 | 4/2010 | Kahn et al. |
| 7,713,173 B2 | 5/2010 | Shin et al. |
| 7,762,952 B2 | 7/2010 | Lee et al. |
| 7,771,320 B2 | 8/2010 | Riley et al. |
| 7,774,156 B2 | 8/2010 | Niva et al. |
| 7,789,802 B2 | 9/2010 | Lee et al. |
| 7,881,902 B1 | 2/2011 | Kahn et al. |
| 7,927,253 B2 | 4/2011 | Vincent et al. |
| 7,942,824 B1 | 5/2011 | Kayyali et al. |
| 7,953,549 B2 | 5/2011 | Graham et al. |
| 7,983,876 B2 | 7/2011 | Vock et al. |
| 8,005,922 B2 | 8/2011 | Boudreau et al. |
| 8,028,443 B2 | 10/2011 | Case, Jr. |
| 8,055,469 B2 | 11/2011 | Kulach et al. |
| 8,099,318 B2 | 1/2012 | Moukas et al. |
| 8,132,037 B2 | 3/2012 | Fehr et al. |
| 8,177,260 B2 | 5/2012 | Tropper et al. |
| 8,180,591 B2 | 5/2012 | Yuen et al. |
| 8,180,592 B2 | 5/2012 | Yuen et al. |

(56) References Cited

U.S. PATENT DOCUMENTS

| | | |
|---|---|---|
| 8,270,297 B2 | 9/2012 | Akasaka et al. |
| 8,311,769 B2 | 11/2012 | Yuen et al. |
| 8,311,770 B2 | 11/2012 | Yuen et al. |
| 8,386,008 B2 | 2/2013 | Yuen et al. |
| 8,437,980 B2 | 5/2013 | Yuen et al. |
| 8,462,591 B1 | 6/2013 | Marhaben |
| 8,463,576 B2 | 6/2013 | Yuen et al. |
| 8,463,577 B2 | 6/2013 | Yuen et al. |
| 8,487,771 B2 | 7/2013 | Hsieh et al. |
| 8,533,269 B2 | 9/2013 | Brown |
| 8,533,620 B2 | 9/2013 | Hoffman et al. |
| 8,543,185 B2 | 9/2013 | Yuen et al. |
| 8,543,351 B2 | 9/2013 | Yuen et al. |
| 8,548,770 B2 | 10/2013 | Yuen et al. |
| 8,562,489 B2 | 10/2013 | Burton et al. |
| 8,583,402 B2 | 11/2013 | Yuen et al. |
| 8,597,093 B2 | 12/2013 | Engelberg et al. |
| 8,634,796 B2 | 1/2014 | Johnson |
| 8,670,953 B2 | 3/2014 | Yuen et al. |
| 8,684,900 B2 | 4/2014 | Tran |
| 8,690,578 B1 | 4/2014 | Nusbaum et al. |
| 8,738,321 B2 | 5/2014 | Yuen et al. |
| 8,738,323 B2 | 5/2014 | Yuen et al. |
| 8,744,803 B2 | 6/2014 | Park et al. |
| 8,762,101 B2 | 6/2014 | Yuen et al. |
| 8,764,651 B2 | 7/2014 | Tran |
| 8,847,988 B2 | 9/2014 | Geisner et al. |
| 8,868,377 B2 | 10/2014 | Yuen et al. |
| 8,949,070 B1 | 2/2015 | Kahn et al. |
| 8,954,290 B2 | 2/2015 | Yuen et al. |
| 8,968,195 B2 | 3/2015 | Tran |
| 9,047,648 B1 | 6/2015 | Lekutai et al. |
| 9,185,100 B1 * | 11/2015 | Juels .................... H04W 4/023 |
| 9,743,443 B2 | 8/2017 | Panther |
| 2001/0049470 A1 | 12/2001 | Mault et al. |
| 2001/0055242 A1 | 12/2001 | Deshmuhk et al. |
| 2002/0013717 A1 | 1/2002 | Ando et al. |
| 2002/0019585 A1 | 2/2002 | Dickenson |
| 2002/0077219 A1 | 6/2002 | Cohen et al. |
| 2002/0082144 A1 | 6/2002 | Pfeffer |
| 2002/0087264 A1 | 7/2002 | Hills et al. |
| 2002/0109600 A1 | 8/2002 | Mault et al. |
| 2002/0178060 A1 | 11/2002 | Sheehan |
| 2002/0191797 A1 | 12/2002 | Perlman |
| 2002/0198776 A1 | 12/2002 | Nara et al. |
| 2003/0018523 A1 | 1/2003 | Rappaport et al. |
| 2003/0050537 A1 | 3/2003 | Wessel |
| 2003/0065561 A1 | 4/2003 | Brown et al. |
| 2003/0131059 A1 | 7/2003 | Brown et al. |
| 2003/0171189 A1 | 9/2003 | Kaufman |
| 2004/0054497 A1 | 3/2004 | Kurtz |
| 2004/0061324 A1 | 4/2004 | Howard |
| 2004/0117963 A1 | 6/2004 | Schneider |
| 2004/0122488 A1 | 6/2004 | Mazar |
| 2004/0152957 A1 | 8/2004 | Stivoric et al. |
| 2004/0239497 A1 | 12/2004 | Schwartzman et al. |
| 2004/0249299 A1 | 12/2004 | Cobb |
| 2004/0257557 A1 | 12/2004 | Block |
| 2005/0037844 A1 | 2/2005 | Shum et al. |
| 2005/0038679 A1 | 2/2005 | Short |
| 2005/0054938 A1 | 3/2005 | Wehman et al. |
| 2005/0102172 A1 | 5/2005 | Sirmans, Jr. |
| 2005/0107723 A1 | 5/2005 | Wehman et al. |
| 2005/0163056 A1 | 7/2005 | Ranta-Aho et al. |
| 2005/0171410 A1 | 8/2005 | Hjelt et al. |
| 2005/0186965 A1 | 8/2005 | Paconis et al. |
| 2005/0187481 A1 | 8/2005 | Hatib |
| 2005/0195830 A1 | 9/2005 | Chitrapu et al. |
| 2005/0216724 A1 | 9/2005 | Isozaki |
| 2005/0228244 A1 | 10/2005 | Banet |
| 2005/0228692 A1 | 10/2005 | Hodgdon |
| 2005/0234742 A1 | 10/2005 | Hodgdon |
| 2005/0248718 A1 | 11/2005 | Howell et al. |
| 2005/0272564 A1 | 12/2005 | Pyles et al. |
| 2006/0004265 A1 | 1/2006 | Pulkkinen et al. |
| 2006/0020174 A1 | 1/2006 | Matsumura |
| 2006/0020177 A1 | 1/2006 | Seo et al. |
| 2006/0025282 A1 | 2/2006 | Redmann |
| 2006/0039348 A1 | 2/2006 | Racz et al. |
| 2006/0047208 A1 | 3/2006 | Yoon |
| 2006/0047447 A1 | 3/2006 | Brady et al. |
| 2006/0064276 A1 | 3/2006 | Ren et al. |
| 2006/0069619 A1 | 3/2006 | Walker et al. |
| 2006/0089542 A1 | 4/2006 | Sands |
| 2006/0111944 A1 | 5/2006 | Sirmans, Jr. et al. |
| 2006/0129436 A1 | 6/2006 | Short |
| 2006/0143645 A1 | 6/2006 | Vock et al. |
| 2006/0166718 A1 | 7/2006 | Seshadri et al. |
| 2006/0217231 A1 | 9/2006 | Parks et al. |
| 2006/0247952 A1 | 11/2006 | Muraca |
| 2006/0277474 A1 | 12/2006 | Robarts et al. |
| 2006/0281409 A1 * | 12/2006 | Levien .................... H04W 4/08 455/41.2 |
| 2006/0282021 A1 | 12/2006 | DeVaul et al. |
| 2006/0287883 A1 | 12/2006 | Turgiss et al. |
| 2006/0288117 A1 | 12/2006 | Raveendran et al. |
| 2007/0011028 A1 | 1/2007 | Sweeney |
| 2007/0049384 A1 | 3/2007 | Kinq et al. |
| 2007/0050715 A1 | 3/2007 | Behar |
| 2007/0051369 A1 | 3/2007 | Choi et al. |
| 2007/0061593 A1 | 3/2007 | Celikkan et al. |
| 2007/0071643 A1 | 3/2007 | Hall et al. |
| 2007/0072156 A1 | 3/2007 | Kaufman et al. |
| 2007/0083095 A1 | 4/2007 | Rippo et al. |
| 2007/0083602 A1 | 4/2007 | Heogenhouqen et al. |
| 2007/0123165 A1 * | 5/2007 | Sheynman .......... H04M 1/7253 455/41.2 |
| 2007/0123391 A1 | 5/2007 | Shin et al. |
| 2007/0135264 A1 | 6/2007 | Rosenberq |
| 2007/0136093 A1 | 6/2007 | Rankin et al. |
| 2007/0141989 A1 * | 6/2007 | Flinchem .............. H04W 48/20 455/41.2 |
| 2007/0146116 A1 | 6/2007 | Kimbrell |
| 2007/0155277 A1 | 7/2007 | Amitai et al. |
| 2007/0159926 A1 | 7/2007 | Prstojevich et al. |
| 2007/0179356 A1 | 8/2007 | Wessel |
| 2007/0194066 A1 | 8/2007 | Ishihara et al. |
| 2007/0197920 A1 | 8/2007 | Adams |
| 2007/0208544 A1 | 9/2007 | Kulach et al. |
| 2007/0276271 A1 | 11/2007 | Chan |
| 2007/0288265 A1 | 12/2007 | Quinian et al. |
| 2008/0001735 A1 | 1/2008 | Tran |
| 2008/0014947 A1 | 1/2008 | Carnall |
| 2008/0022089 A1 | 1/2008 | Leedom |
| 2008/0032864 A1 | 2/2008 | Hakki |
| 2008/0044014 A1 | 2/2008 | Corndorf |
| 2008/0054072 A1 | 3/2008 | Katracadda et al. |
| 2008/0057890 A1 * | 3/2008 | McKillop ............. G06F 21/445 455/185.1 |
| 2008/0084823 A1 | 4/2008 | Akasaka et al. |
| 2008/0093838 A1 | 4/2008 | Trapper et al. |
| 2008/0097550 A1 | 4/2008 | Dicks et al. |
| 2008/0114829 A1 | 5/2008 | Button et al. |
| 2008/0125288 A1 | 5/2008 | Case |
| 2008/0129457 A1 | 6/2008 | Ritter et al. |
| 2008/0134102 A1 | 6/2008 | Movold et al. |
| 2008/0140163 A1 | 6/2008 | Keacher et al. |
| 2008/0140338 A1 | 6/2008 | No et al. |
| 2008/0146892 A1 | 6/2008 | LeBoeuf et al. |
| 2008/0155077 A1 | 6/2008 | James |
| 2008/0176655 A1 | 7/2008 | James et al. |
| 2008/0275309 A1 | 11/2008 | Stivoric et al. |
| 2008/0287751 A1 | 11/2008 | Stivoric et al. |
| 2008/0320190 A1 * | 12/2008 | Lydon .................. G06F 13/387 710/106 |
| 2008/0320587 A1 * | 12/2008 | Vauclair .................. H04L 41/28 726/17 |
| 2009/0018797 A1 | 1/2009 | Kasama et al. |
| 2009/0034591 A1 | 2/2009 | Julian |
| 2009/0043531 A1 | 2/2009 | Kahn et al. |
| 2009/0047645 A1 | 2/2009 | Dibenedetto et al. |
| 2009/0048044 A1 | 2/2009 | Oleson et al. |
| 2009/0054737 A1 | 2/2009 | Magar et al. |
| 2009/0054751 A1 | 2/2009 | Babashan et al. |

(56) References Cited

U.S. PATENT DOCUMENTS

| | | |
|---|---|---|
| 2009/0058635 A1 | 3/2009 | LaLonde |
| 2009/0063193 A1 | 3/2009 | Barton et al. |
| 2009/0063293 A1 | 3/2009 | Mirrashidi et al. |
| 2009/0093341 A1 | 4/2009 | James et al. |
| 2009/0098821 A1 | 4/2009 | Shinya |
| 2009/0143012 A1* | 6/2009 | Jeon .................... H04W 52/50 455/41.2 |
| 2009/0144456 A1 | 6/2009 | Gelf et al. |
| 2009/0144639 A1 | 6/2009 | Nims et al. |
| 2009/0150178 A1 | 6/2009 | Sutton et al. |
| 2009/0156172 A1 | 6/2009 | Chan |
| 2009/0171788 A1 | 7/2009 | Trapper et al. |
| 2009/0195350 A1 | 8/2009 | Tsern et al. |
| 2009/0240814 A1* | 9/2009 | Brubacher .............. H04W 8/18 709/227 |
| 2009/0262088 A1 | 10/2009 | Moll-Carrillo et al. |
| 2009/0264713 A1 | 10/2009 | Van Loenen et al. |
| 2009/0271147 A1 | 10/2009 | Sugai |
| 2009/0287921 A1 | 11/2009 | Zhu |
| 2009/0307517 A1 | 12/2009 | Fehr et al. |
| 2009/0309742 A1 | 12/2009 | Alexander et al. |
| 2010/0023348 A1 | 1/2010 | Hardee et al. |
| 2010/0045425 A1 | 2/2010 | Chivallier |
| 2010/0058064 A1* | 3/2010 | Kirovski ............... H04L 9/3073 713/176 |
| 2010/0059561 A1 | 3/2010 | Ellis et al. |
| 2010/0069203 A1 | 3/2010 | Kawaguchi et al. |
| 2010/0125729 A1 | 5/2010 | Baentsch |
| 2010/0130873 A1 | 5/2010 | Yuen et al. |
| 2010/0153709 A1 | 6/2010 | Thomas et al. |
| 2010/0158494 A1 | 6/2010 | Kine |
| 2010/0167783 A1 | 7/2010 | Alameh et al. |
| 2010/0179411 A1 | 7/2010 | Holmstrom et al. |
| 2010/0185064 A1 | 7/2010 | Bandic et al. |
| 2010/0205541 A1 | 8/2010 | Rapaport et al. |
| 2010/0217099 A1 | 8/2010 | LeBoeuf et al. |
| 2010/0222000 A1* | 9/2010 | Sauer .................... G06F 9/451 455/41.2 |
| 2010/0222179 A1 | 9/2010 | Temple et al. |
| 2010/0261987 A1 | 10/2010 | Kamath et al. |
| 2010/0262696 A1 | 10/2010 | Oshiba |
| 2010/0292050 A1 | 11/2010 | DiBenedetto |
| 2010/0292556 A1 | 11/2010 | Golden |
| 2010/0292600 A1 | 11/2010 | DiBenedetto et al. |
| 2010/0295684 A1 | 11/2010 | Hsieh et al. |
| 2010/0298661 A1 | 11/2010 | McCombie et al. |
| 2010/0304674 A1* | 12/2010 | Kim .................... H04W 76/10 455/41.2 |
| 2010/0311544 A1 | 12/2010 | Robinette et al. |
| 2010/0318578 A1* | 12/2010 | Treu .................... G06F 19/3418 707/802 |
| 2010/0331145 A1* | 12/2010 | Lakovic ................ G04F 10/00 482/8 |
| 2011/0003665 A1 | 1/2011 | Burton et al. |
| 2011/0009051 A1 | 1/2011 | Khedouri et al. |
| 2011/0021143 A1 | 1/2011 | Kapur |
| 2011/0022349 A1 | 1/2011 | Stirling et al. |
| 2011/0063103 A1* | 3/2011 | Lee .................... H04M 1/6066 340/505 |
| 2011/0080349 A1 | 4/2011 | Holbein et al. |
| 2011/0087076 A1 | 4/2011 | Brynelsen et al. |
| 2011/0106449 A1 | 5/2011 | Chowdhary et al. |
| 2011/0131005 A1 | 6/2011 | Ueshima et al. |
| 2011/0131406 A1 | 6/2011 | Jones |
| 2011/0145894 A1 | 6/2011 | Garcia Morchon |
| 2011/0153773 A1 | 6/2011 | Vandwalle |
| 2011/0167262 A1 | 7/2011 | Ross et al. |
| 2011/0193704 A1 | 8/2011 | Harper et al. |
| 2011/0197157 A1 | 8/2011 | Hoffman et al. |
| 2011/0214030 A1 | 9/2011 | Greenberg et al. |
| 2011/0221590 A1 | 9/2011 | Baker |
| 2011/0224508 A1 | 9/2011 | Moon |
| 2011/0230729 A1 | 9/2011 | Shirasaki et al. |
| 2011/0258689 A1* | 10/2011 | Cohen .................... H04L 63/061 726/7 |
| 2011/0263201 A1* | 10/2011 | Bukurak ................ H04W 4/00 455/41.2 |
| 2012/0035487 A1 | 2/2012 | Werner et al. |
| 2012/0044057 A1* | 2/2012 | Kang .................... H04L 63/10 340/10.4 |
| 2012/0072165 A1 | 3/2012 | Jallon |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0092157 A1 | 4/2012 | Tran |
| 2012/0094649 A1 | 4/2012 | Porrati et al. |
| 2012/0102008 A1 | 4/2012 | Kaariainen et al. |
| 2012/0116684 A1 | 5/2012 | Ingrassia, Jr. et al. |
| 2012/0119911 A1 | 5/2012 | Jeon et al. |
| 2012/0165684 A1 | 6/2012 | Sholder |
| 2012/0166257 A1 | 6/2012 | Shiraqami et al. |
| 2012/0179278 A1 | 7/2012 | Riley et al. |
| 2012/0183939 A1 | 7/2012 | Aragones et al. |
| 2012/0215328 A1 | 8/2012 | Schmelzer |
| 2012/0226471 A1 | 9/2012 | Yuen et al. |
| 2012/0226472 A1 | 9/2012 | Yuen et al. |
| 2012/0227737 A1 | 9/2012 | Mastrototaro et al. |
| 2012/0239221 A1* | 9/2012 | Mighdoll ............ G05D 23/1902 700/300 |
| 2012/0254987 A1* | 10/2012 | Ge .................... H04L 63/0492 726/19 |
| 2012/0265480 A1 | 10/2012 | Oshima |
| 2012/0274508 A1 | 11/2012 | Brown et al. |
| 2012/0283855 A1 | 11/2012 | Hoffman et al. |
| 2012/0296400 A1 | 11/2012 | Bierman et al. |
| 2012/0297229 A1 | 11/2012 | Desai et al. |
| 2012/0316456 A1 | 12/2012 | Rahman et al. |
| 2012/0324226 A1 | 12/2012 | Bichsel et al. |
| 2012/0330109 A1 | 12/2012 | Tran |
| 2013/0006718 A1 | 1/2013 | Nielsen et al. |
| 2013/0041590 A1 | 2/2013 | Burich et al. |
| 2013/0072169 A1 | 3/2013 | Ross et al. |
| 2013/0073254 A1 | 3/2013 | Yuen et al. |
| 2013/0073255 A1 | 3/2013 | Yuen et al. |
| 2013/0080113 A1 | 3/2013 | Yuen et al. |
| 2013/0094600 A1 | 4/2013 | Beziat et al. |
| 2013/0095459 A1 | 4/2013 | Tran |
| 2013/0095753 A1* | 4/2013 | Chen .................... H04W 76/10 455/41.1 |
| 2013/0096843 A1 | 4/2013 | Yuen et al. |
| 2013/0102251 A1 | 4/2013 | Linde et al. |
| 2013/0103847 A1 | 4/2013 | Brown |
| 2013/0106684 A1 | 5/2013 | Weast |
| 2013/0132501 A1 | 5/2013 | Vandwalle et al. |
| 2013/0151196 A1 | 6/2013 | Yuen et al. |
| 2013/0158369 A1 | 6/2013 | Yuen et al. |
| 2013/0166048 A1 | 6/2013 | Werner et al. |
| 2013/0185559 A1* | 7/2013 | Morel .................... H04L 63/18 713/168 |
| 2013/0190903 A1 | 7/2013 | Balakrishnan et al. |
| 2013/0191034 A1 | 7/2013 | Weast et al. |
| 2013/0203475 A1 | 8/2013 | Kil et al. |
| 2013/0209972 A1 | 8/2013 | Carter et al. |
| 2013/0225117 A1 | 8/2013 | Giacoletto et al. |
| 2013/0228063 A1 | 9/2013 | Turner |
| 2013/0231574 A1 | 9/2013 | Tran |
| 2013/0238287 A1 | 9/2013 | Hoffman et al. |
| 2013/0261475 A1 | 10/2013 | Mochizuki |
| 2013/0267249 A1 | 10/2013 | Rosenberg |
| 2013/0268199 A1 | 10/2013 | Nielsen et al. |
| 2013/0268236 A1 | 10/2013 | Yuen et al. |
| 2013/0268687 A1 | 10/2013 | Schrecker |
| 2013/0268767 A1 | 10/2013 | Schrecker |
| 2013/0274904 A1 | 10/2013 | Coza et al. |
| 2013/0281110 A1 | 10/2013 | Zelinka |
| 2013/0289366 A1 | 10/2013 | Chua et al. |
| 2013/0296666 A1 | 11/2013 | Kumar et al. |
| 2013/0296672 A1 | 11/2013 | O'Neil et al. |
| 2013/0296673 A1 | 11/2013 | Thaveeprungsriporn et al. |

(56) References Cited

U.S. PATENT DOCUMENTS

| | | |
|---|---|---|
| 2013/0310896 A1 | 11/2013 | Mass |
| 2013/0325396 A1 | 12/2013 | Yuen et al. |
| 2013/0331058 A1 | 12/2013 | Harvey |
| 2014/0035761 A1 | 2/2014 | Burton et al. |
| 2014/0039804 A1 | 2/2014 | Park et al. |
| 2014/0039840 A1 | 2/2014 | Yuen et al. |
| 2014/0039841 A1 | 2/2014 | Yuen et al. |
| 2014/0052280 A1 | 2/2014 | Yuen et al. |
| 2014/0067278 A1 | 3/2014 | Yuen et al. |
| 2014/0077673 A1 | 3/2014 | Garg et al. |
| 2014/0094941 A1 | 4/2014 | Ellis et al. |
| 2014/0125618 A1 | 5/2014 | Panther et al. |
| 2014/0164611 A1 | 6/2014 | Molettiere et al. |
| 2014/0180022 A1 | 6/2014 | Stivoric et al. |
| 2014/0207264 A1 | 7/2014 | Quy |
| 2014/0213858 A1 | 7/2014 | Presura et al. |
| 2014/0275885 A1 | 9/2014 | Isaacson et al. |
| 2014/0278229 A1 | 9/2014 | Hong et al. |
| 2014/0316305 A1 | 10/2014 | Venkatraman et al. |
| 2014/0337621 A1 | 11/2014 | Nakhimov |
| 2015/0026647 A1 | 1/2015 | Park et al. |
| 2016/0255461 A1* | 9/2016 | Zerr .................. H04W 76/10 455/41.3 |

FOREIGN PATENT DOCUMENTS

| | | |
|---|---|---|
| WO | WO 02/011019 | 2/2002 |
| WO | WO 06/055125 | 5/2006 |
| WO | WO 06/090197 | 8/2006 |
| WO | WO 08/038141 | 4/2008 |
| WO | WO 09/042965 | 4/2009 |
| WO | WO 12/061438 | 5/2012 |
| WO | WO 12/170586 | 12/2012 |
| WO | WO 12/170924 | 12/2012 |
| WO | WO 12/171032 | 12/2012 |
| WO | WO 15/127067 | 8/2015 |
| WO | WO 16/003269 | 1/2016 |

OTHER PUBLICATIONS

"Fitbit automatically tracks your fitness and sleep," Fitbit Inc., published online at www.fitbit.com, downloaded Sep. 10, 2008, 1 page.

"SCP1000-D01/D11 Pressure Sensor as Barometer and Altimeter," VTI Technologies Oy, Application Note 33, date unknown but not later than Nov. 3, 2011, 3 pages.

"Suunto LUMI User Guide," Suunto Oy, Sep. 2007, 49 pages.

"Using MS5534 for altimeters and barometers," Intersema Sensoric SA, Intersema Application Note AN501, date unknown but not later than Nov. 3, 2011, 12 pages.

Clifford et al., "Altimeter and Barometer System," Freescale Semiconductor, Inc., Freescale Semiconductor Application Note AN1979, Rev 3, Nov. 2006.

Fang et al., "Design of a Wireless Assisted Pedestrian Dead Reckoning System—The NavMote Experience," IEEE Transactions on Instrumentation and Measurement, vol. 54, No. 6, Dec. 2005, pp. 2342-2358.

Godfrey et al., "Direct measurement of human movement by accelerometry," Medical Engineering & Physics, vol. 30, 2008, pp. 1364-1386.

Godha et al., "Foot mounted inertial system for pedestrian navigation," Measurement Science and Technology, vol. 19, No. 7, May 2008, pp. 1-9.

Ladetto et al., "On Foot Navigation: When GPS alone is not enough," Journal of Navigation, vol. 53, No. 2, Sep. 2000, pp. 279-285.

Lammel et al., "Indoor Navigation with MEMS sensors," Proceedings of the Eurosensors XXIII Conference, vol. 1, No. 1, Sep. 2009, pp. 532-535.

Lester et al., "A Hybrid Discriminative/Generative Approach for Modeling Human Activities," Proceedings of the International Joint Conference on Artificial Intelligence, 2005, pp. 766-772.

Lester et al., "Validated caloric expenditure estimation using a single body-worn sensor," Proceedings of the International Conference on Ubiquitous Computing, 2009, pp. 225-234.

Ohtaki et al., Automatic classification of ambulatory movements and evaluation of energy consumptions utilizing accelerometers and a barometer, Microsystem Technologies, vol. 11, No. 8-10, Aug. 2005, pp. 1034-1040.

Parkka et al., "Activity Classification Using Realistic Data From Wearable Sensors," IEEE Transactions on Information Technology in Biomedicine, vol. 10, No. 1, Jan. 2006, pp. 119-128.

Perrin et al., "Improvement of walking speed prediction by accelerometry and altimetry, validated by satellite positioning," Medical & Biological Engineering & Computing, vol. 38, 2000, pp. 164-168.

Retscher, "An Intelligent Multi-sensor System for Pedestrian Navigation," Journal of Global Positioning Systems, vol. 5, No. 1, 2006, pp. 110-118.

Sagawa et al., "Classification of Human Moving Patterns Using Air Pressure and Acceleration," Proceedings of the 24th Annual Conference of the IEEE Industrial Electronics Society, vol. 2, Aug.-Sep. 1998, pp. 1214-1219.

Sagawa et al., "Non-restricted measurement of walking distance," IEEE International Conference on Systems, Man, and Cybernetics, vol. 3, Oct. 2000, pp. 1847-1852.

Specification of the Bluetooth.RTM. System, Core Package, version 4.1, Dec. 2013, vols. 0 & 1, 282 pages.

Stirling et al., "Evaluation of a New Method of Heading Estimation for Pedestrian Dead Reckoning Using Shoe Mounted Sensors," Journal of Navigation, vol. 58, 2005, pp. 31-45.

Tanigawa et al., "Drift-free dynamic height sensor using MEMS IMU aided by MEMS pressure sensor," Workshop on Positioning, Navigation and Communication, Mar. 2008, pp. 191-196.

International Search Report dated Aug. 15, 2008, in related application PCT/IB07/03617.

* cited by examiner

SECURE PAIRING OF DEVICES VIA PAIRING FACILITATOR-INTERMEDIARY DEVICE

CLAIM OF PRIORITY

This application is a continuation application and claims the benefit of and priority under 35 U.S.C. § 120 to co-pending U.S. application Ser. No. 15/012,552, filed on Feb. 1, 2016, entitled "SECURE PAIRING OF DEVICES VIA PAIRING FACILITATOR-INTERMEDIARY DEVICE", which is a continuation of U.S. application Ser. No. 14/642,352, filed on Mar. 9, 2015, entitled "Secure Pairing of Devices Via Pairing Facilitator-Intermediary Device", now granted as U.S. Pat. No. 9,253,168, which is a continuation application and claims the benefit of and priority under 35 U.S.C. § 120 to U.S. application Ser. No. 13/872,015, filed on Apr. 26, 2013, entitled "Secure Pairing of Devices Via Pairing Facilitator-Intermediary Device", which claims the benefit of and priority under 35 U.S.C. § 119(e) to U.S. Provisional Application Ser. No. 61/638,650, entitled "Secure Pairing of Devices via Pairing Facilitator/Intermediary Device", filed Apr. 26, 2012, all of which are incorporated by reference herein in their entirety.

INTRODUCTION

In one aspect, the present inventions relate to systems and circuitry for and/or methods of establishing communication having one or more pairing facilitator-intermediary devices (for example, a network connected server) to enable or facilitate pairing and/or registering two or more devices (for example, (i) a portable biometric monitoring device and (ii) a smartphone, laptop and/or tablet) to, for example, recognize, interact and/or identify such devices and/or enable interoperability between such devices. In one embodiment, the pairing facilitator-intermediary device responsively communicates data and/or instructions to one or more of the devices (to be paired or registered) which, in response, enable or facilitate such devices to pair or register. The present inventions may be advantageous where one or both of the devices to be paired or registered do not include or employ functionality and/or resident circuitry (for example, an interface (for example, a user interface) or resident communication circuitry) that allows, enables or permits a user to pair and/or register the devices. For example, where the device to be paired or registered do not possess a, or employ its user interface and/or communication circuitry which is suitable for selection, entering and/or communicating data to its counterpart device (for example, via communicating out-of-band data).

Notably, pairing or registering devices may be characterized as enabling interoperability between such devices and/or an initialization process which creates a link (for example, a lasting and/or sustainable link) between two or more devices to facilitate, allow and/or make possible future communication between the devices. After the pairing process is complete, one or more of the devices involved in the pairing process may save information about one or more of the other devices so that when a new, subsequent and/or future communication link is to be set-up, little or no user interaction is required to create the connection. Similarly, registering devices with each other or with a third device allows subsequent and/or future communication between two or more of the devices to occur with little or no user interaction.

In one embodiment, one or more of the devices to be paired or registered is/are portable biometric monitoring device(s). Such portable biometric monitoring device(s) may, according to embodiments described herein, have shapes and/or sizes that are/is adapted for coupling to (for example, secured to, worn, carried or borne by, etc.) the body or clothing of a user and, when worn, do not impede motion, activity or the like of the user. Examples of portable biometric monitoring devices are shown in FIGS. 1-5. Some portable biometric monitoring devices such as those in FIGS. 1-2 may have a display and a button. Other portable biometric monitoring devices may have more limited user interfaces such as those shown in FIGS. 4A, 4B and 5. Indeed, some portable biometric monitoring devices may have little or no user interface features such as displays, indicators, or buttons. In one embodiment, the devices collect one or more types of physiological and/or environmental data from embedded sensors and/or external devices and communicate or relay such information to other devices, including devices capable of serving as an Internet-accessible data sources, thus permitting the collected data to be viewed, for example, using a web browser or network-based application. For example, while the user is wearing a biometric monitoring device, the device may calculate and store the user's step count using one or more sensors. The device then transmits data representative of the user's step count to an account on a web service (for example, www.fitbit.com), computer, mobile phone, or health station where the data may be stored, processed, and visualized by the user. Indeed, the device may measure or calculate a plurality of other physiological metrics in addition to, or in place of, the user's step count.

Notably, other physiological metrics include, but are not limited to, energy expenditure (for example, calorie burn), floors climbed and/or descended, heart rate, heart rate variability, heart rate recovery, location and/or heading (for example, through GPS), elevation, ambulatory speed and/or distance traveled, swimming lap count, bicycle distance and/or speed, blood pressure, blood glucose, skin conduction, skin and/or body temperature, electromyography, electroencephalography, weight, body fat, caloric intake, nutritional intake from food, medication intake, sleep periods (i.e., clock time), sleep phases, sleep quality and/or duration, pH levels, hydration levels, and respiration rate. The device may also measure or calculate metrics related to the environment around the user such as barometric pressure, weather conditions (for example, temperature, humidity, pollen count, air quality, rain/snow conditions, wind speed), light exposure (for example, ambient light, UV light exposure, time and/or duration spent in darkness), noise exposure, radiation exposure, and magnetic field.

Furthermore, the device or the system collating the data streams may calculate metrics derived from this data. For example, the device or system may calculate the user's stress and/or relaxation levels through a combination of heart rate variability, skin conduction, noise pollution, and sleep quality. In another example, the device or system may determine the efficacy of a medical intervention (for example, medication) through the combination of medication intake, sleep and/or activity data. In yet another example, the device or system may determine the efficacy of an allergy medication through the combination of pollen data, medication intake, sleep and/or activity data. These examples are provided for illustration only and are not intended to be limiting or exhaustive. Further embodiments and implementations of sensor devices are described and/or illustrated in U.S. patent application Ser. No. 13/156,304, entitled "Portable Biometric Monitoring Devices and Methods of Operating Same" filed Jun. 8, 2011, which is incorporated herein, in its entirety, by reference.

BRIEF DESCRIPTION OF THE DRAWINGS

In the course of the detailed description to follow, reference will be made to the attached drawings. These drawings show different aspects of the present inventions and, where appropriate, reference numerals illustrating like structures, components, materials and/or elements in different figures are labeled similarly. The various embodiments disclosed herein are illustrated by way of example, and not by way of limitation, in the figures of the accompanying drawings and in which like reference numerals refer to the same and/or similar structures/components/features/elements. It is understood that various combinations of the structures, components, features and/or elements, other than those specifically shown, are contemplated and are within the scope of the present inventions.

Moreover, there are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, certain permutations and combinations are not discussed and/or illustrated separately herein.

The various embodiments disclosed herein are illustrated by way of example, and not by way of limitation, in the figures of the accompanying drawings and in which like reference numerals refer to similar elements and in which:

FIG. 1 illustrates an example of a portable monitoring device.

FIG. 2 illustrates an example of a portable monitoring device having a button and a dead front display.

FIG. 3 illustrates a user extremity mounted portable monitoring device having a button, display, and a band.

FIG. 4A illustrates a portable monitoring device having multiple LED's to display information to the user.

FIG. 4B illustrates a portable monitoring device having multiple LED's to display information to the user.

FIG. 5 illustrates a band case for a portable biometric monitoring device and a portable biometric monitoring device having multiple LED's to display information to the user.

FIG. 6 is a block diagram of an embodiment of a system in which a first device and a second device directly communicate with each other as well as communicate with a pairing facilitator-intermediary device to enable and implement a pairing or registering process.

FIG. 7 is a block diagram of an embodiment of a system in which the first device bi-directionally communicates with the pairing facilitator-intermediary device and the second device receives data and/or instructions from the pairing facilitator-intermediary device, and the first and second devices communicate with each other to implement the pairing or registering process.

FIG. 8 is a block diagram of an embodiment of a system in which the first device communicates with the pairing facilitator-intermediary device and the second device sends data to the pairing facilitator-intermediary device, and the first and second communicate to implement the pairing or registering process.

FIG. 9 is a block diagram of an embodiment of a system in which the first device communicates with the pairing facilitator-intermediary device and the first and second devices communicate to implement the pairing or registering process.

FIG. 10 illustrates, in block diagram form, an embodiment having a first device, second device, third device and facilitator-intermediary device wherein the interaction between the first device and second device with each other and with a pairing facilitator-intermediary device occurs to facilitate pairing or registering processes.

Figure 11:
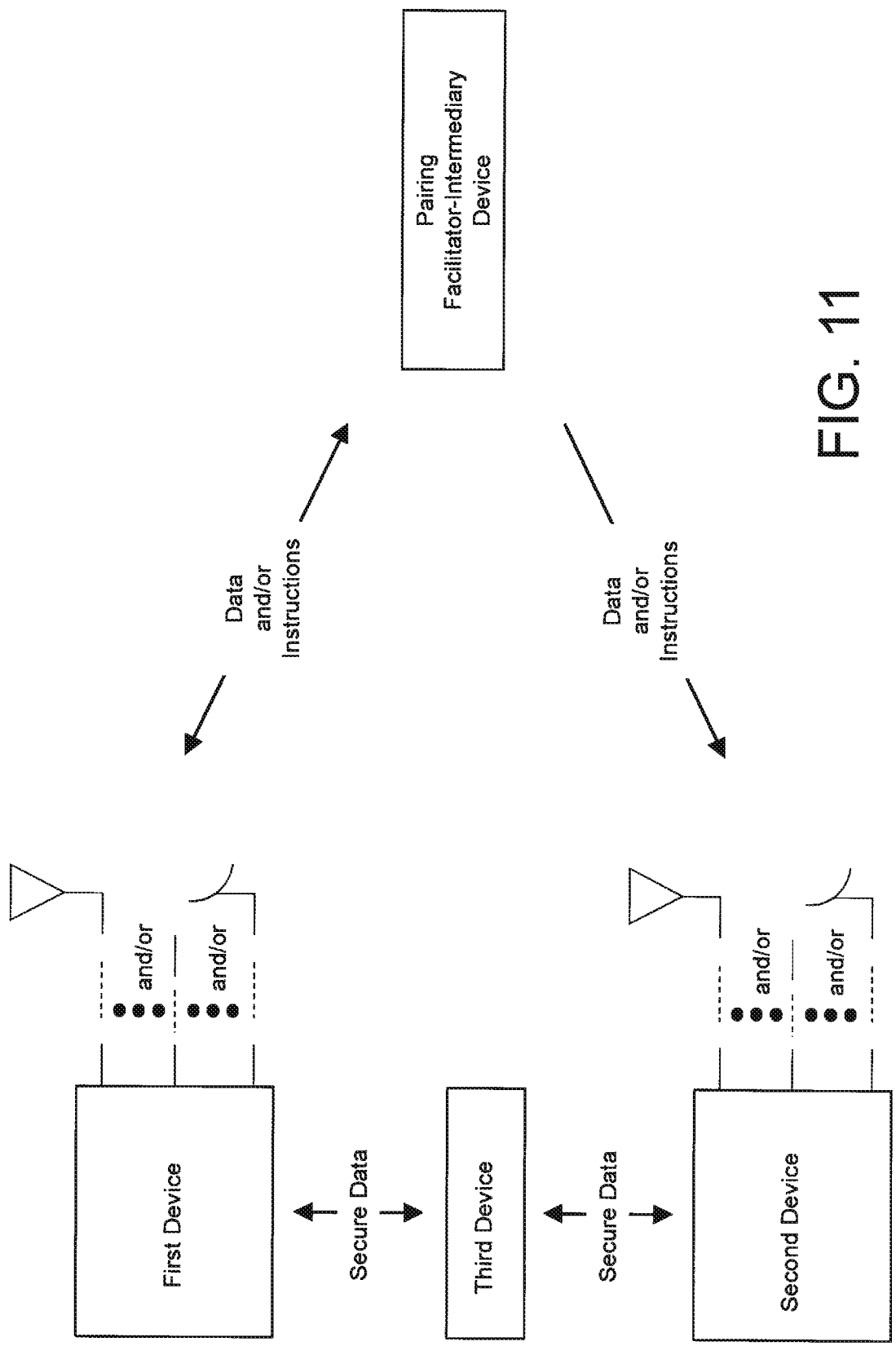

FIG. 11 illustrates, in block diagram form, an embodiment having a first device, second device, third device and facilitator-intermediary device wherein the interaction between the first device and second device with each other and with a pairing facilitator-intermediary device occurs to facilitate pairing or registering processes.

Figure 12:
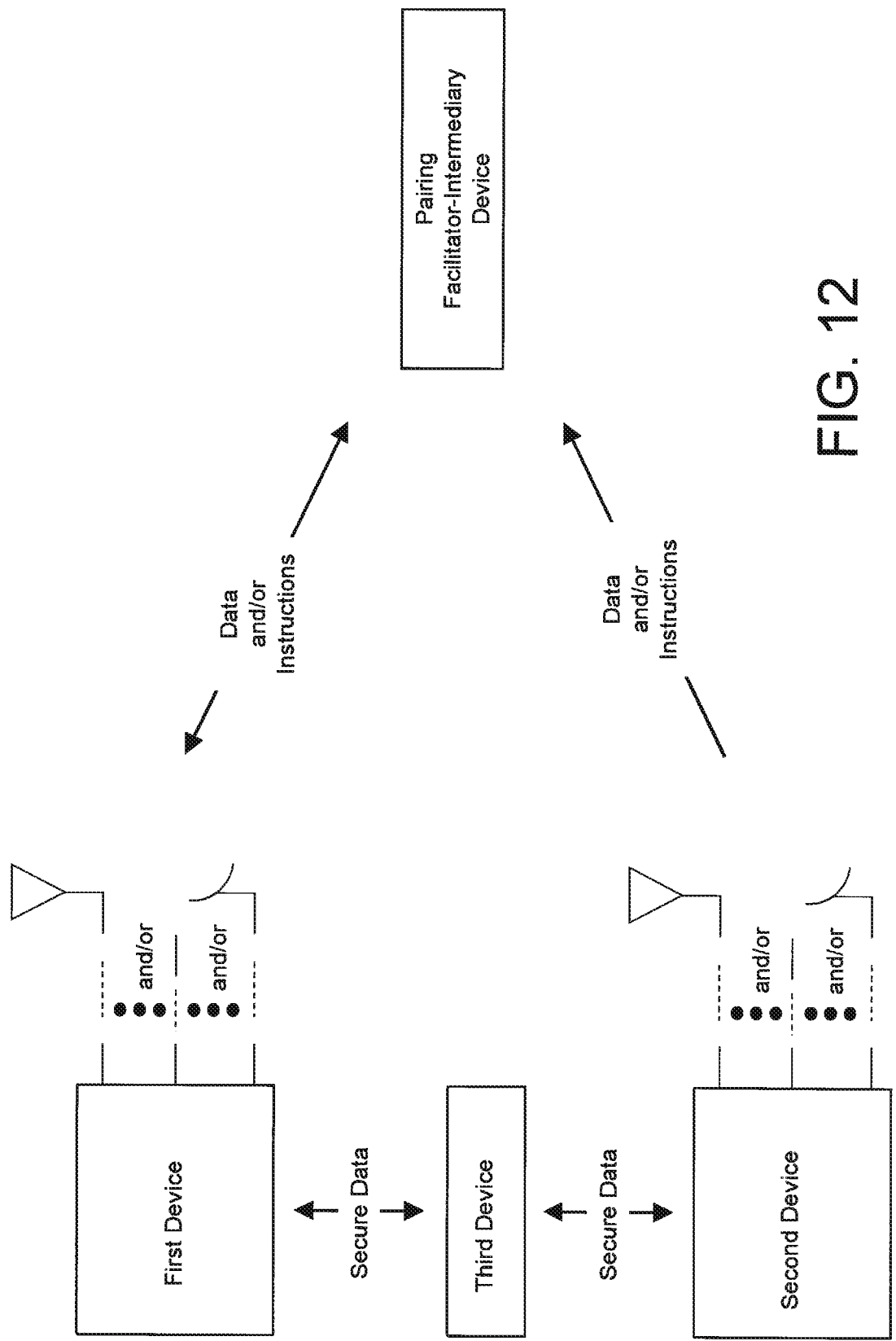

FIG. 12 illustrates, in block diagram form, an embodiment having a first device, second device, third device and facilitator-intermediary device wherein the interaction between the first device and second device with each other and with a pairing facilitator-intermediary device occurs to facilitate pairing or registering processes.

Figure 13:
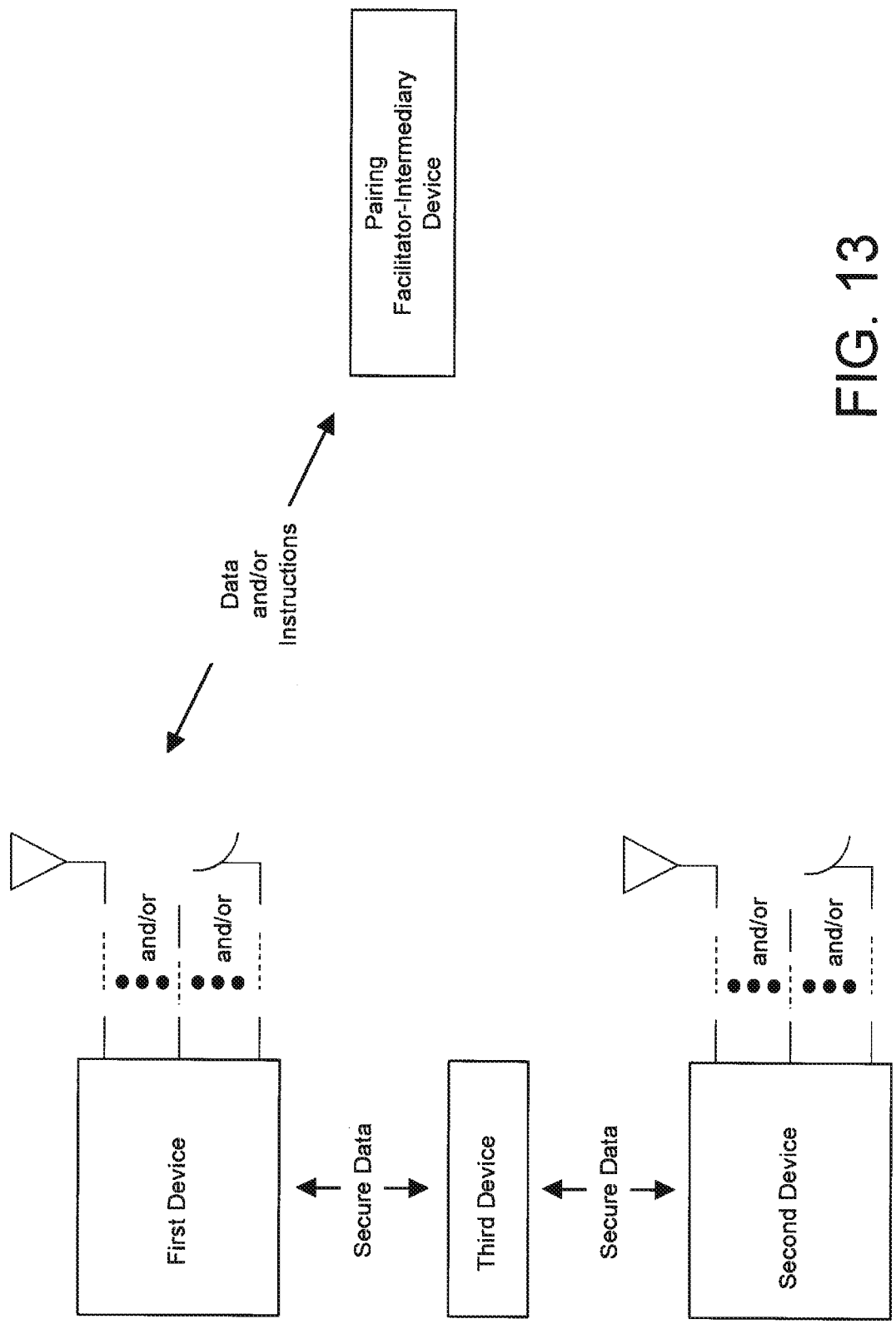

FIG. 13 illustrates, in block diagram form, an embodiment having a first device, second device, third device and facilitator-intermediary device wherein the interaction between the first device and second device with each other and with a pairing facilitator-intermediary device occurs to facilitate pairing or registering processes.

Figure 14:
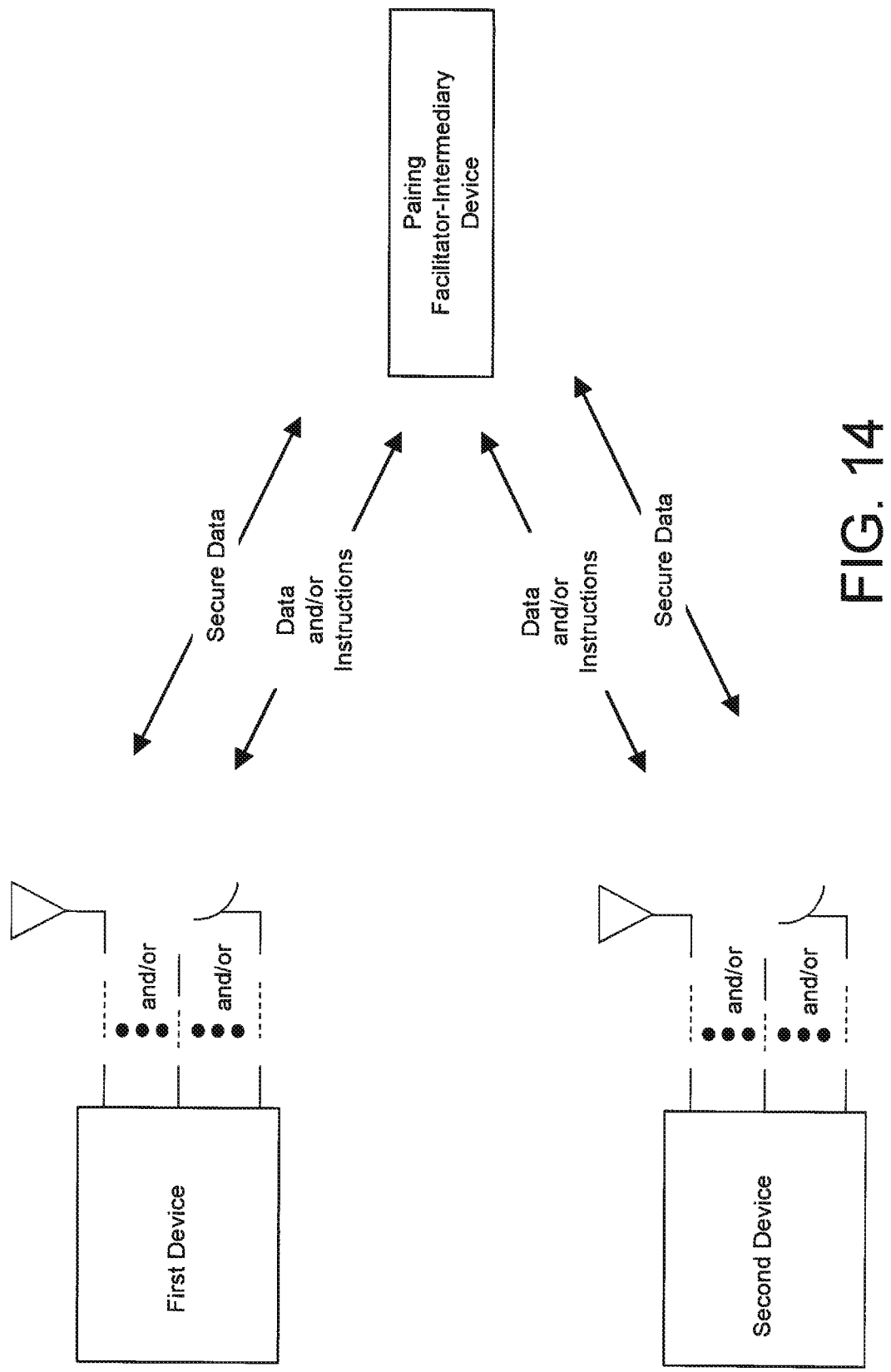

FIG. 14 is a block diagram of an embodiment having a first device, second device and facilitator-intermediary device wherein the interaction between the first device and second device with a pairing facilitator-intermediary device facilitates pairing or registering processes.

Figure 15A:
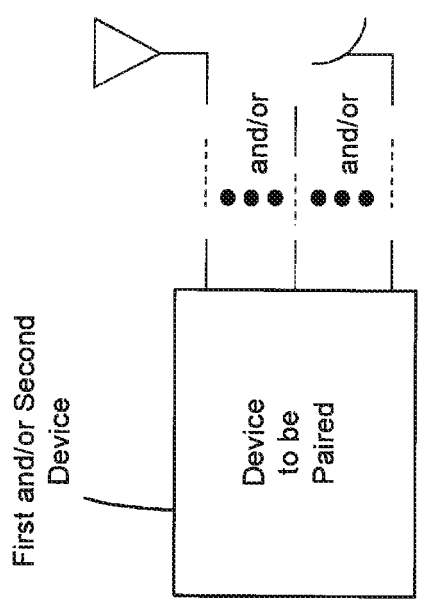

FIG. 15A illustrates, in block diagram form, a first and/or second device(s) to be paired, notably, the device may communicate using any technique, protocols and/or circuitry now known or later developed including wireless, wired and optical techniques.

Figure 15B:
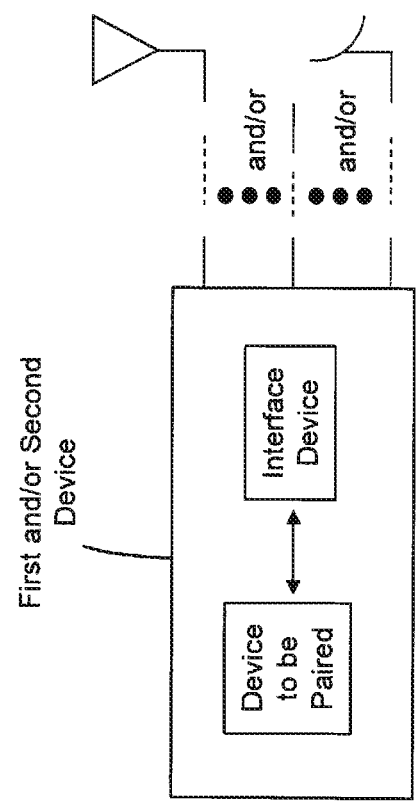

FIG. 15B illustrates, in block diagram form, a first and/or second device(s) having a device to be paired and an interface device.

Figure 15C:
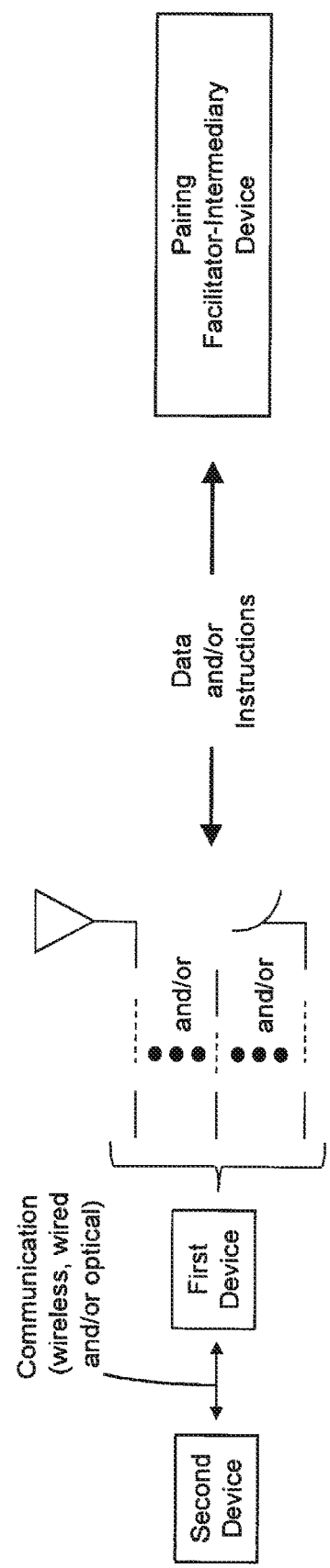

FIG. 15C illustrates, in block diagram form, first and second devices, according to embodiments of the present inventions, second device uses circuitry in the first device to communicate with the pairing facilitator-intermediary device.

Figure 16:
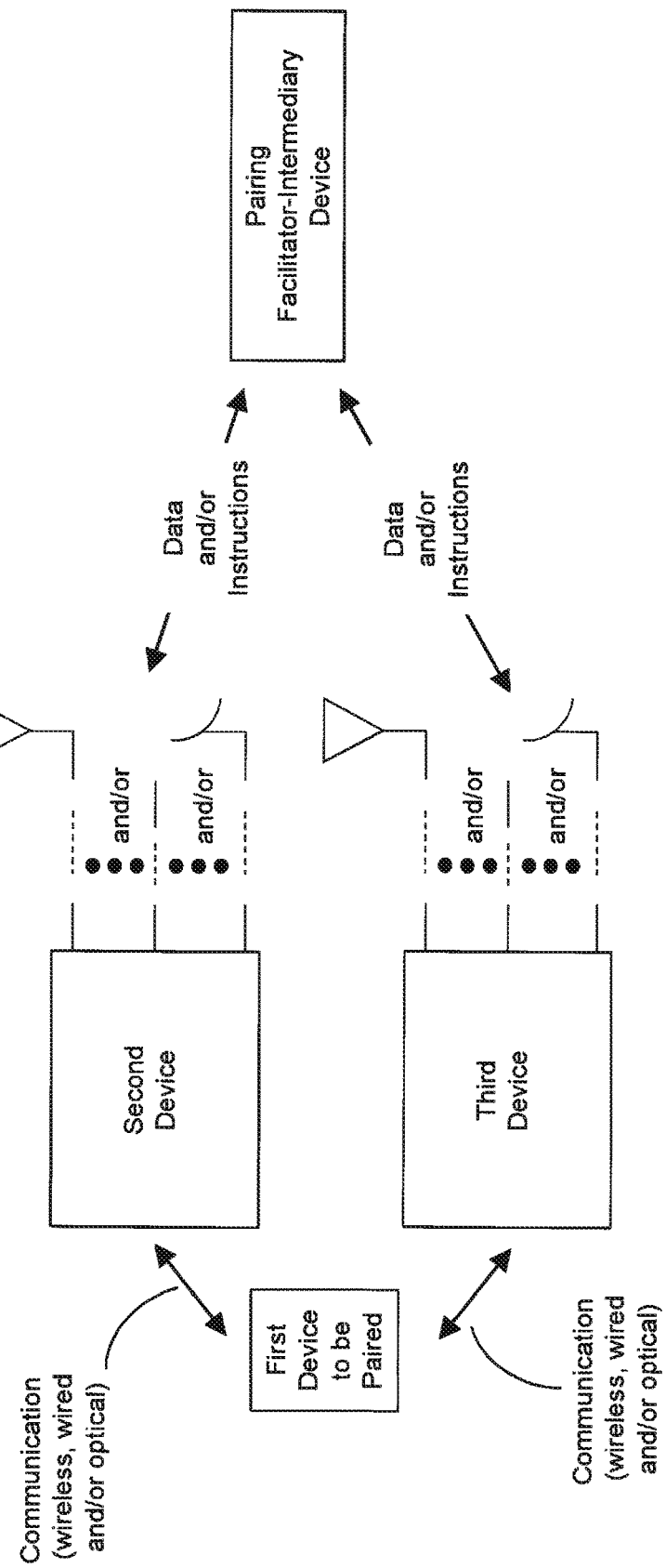

FIG. 16 illustrates, in block diagram form, an embodiment where a first device is already paired to a second device, but is to be paired to a third device.

Figure 17:
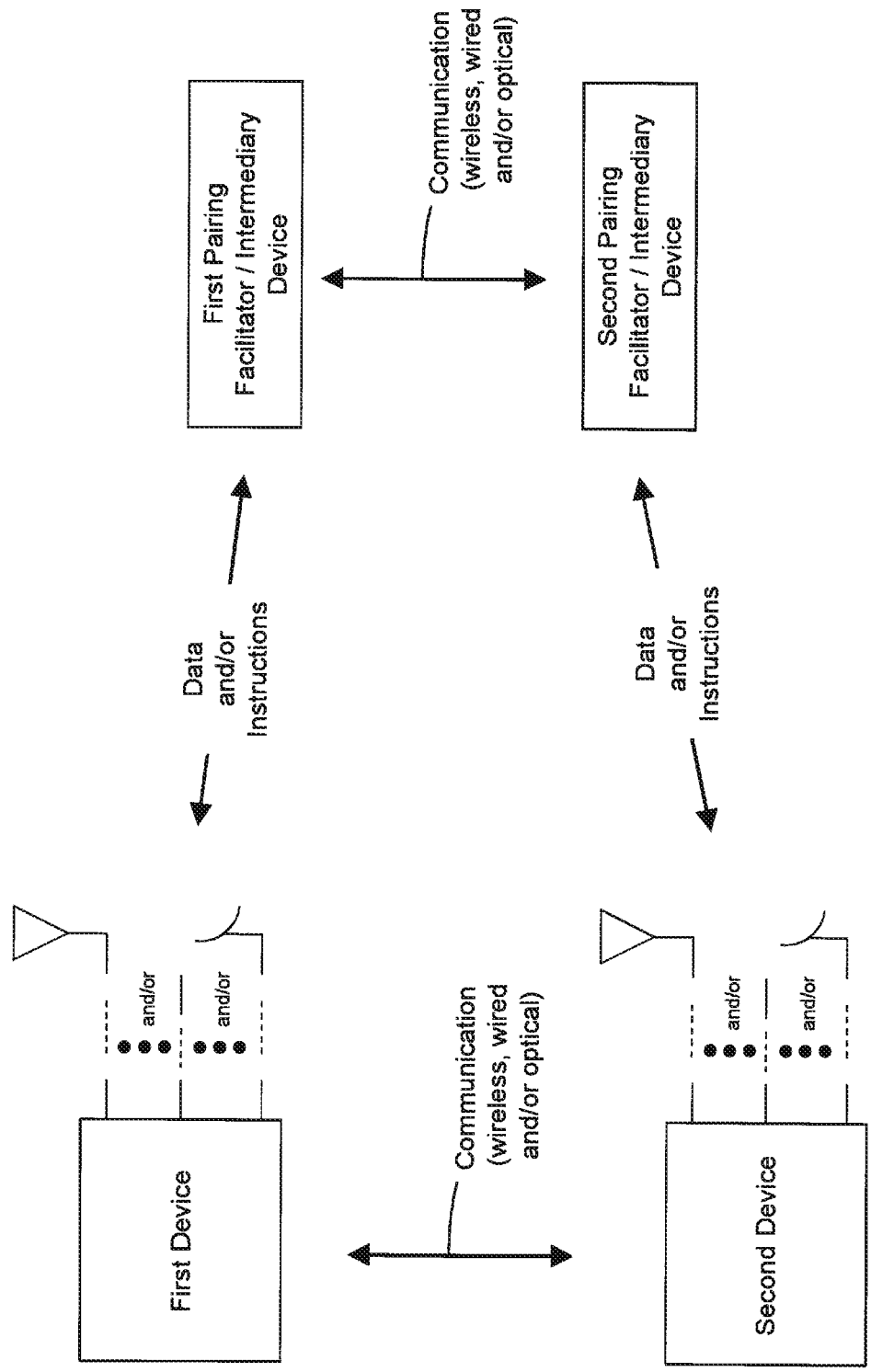

FIG. 17 illustrates an embodiment where multiple pairing facilitator-intermediary devices in communication with each other may send and/or receive data and/or instructions with a first and/or second device.

DETAILED DESCRIPTION

Figure 1:
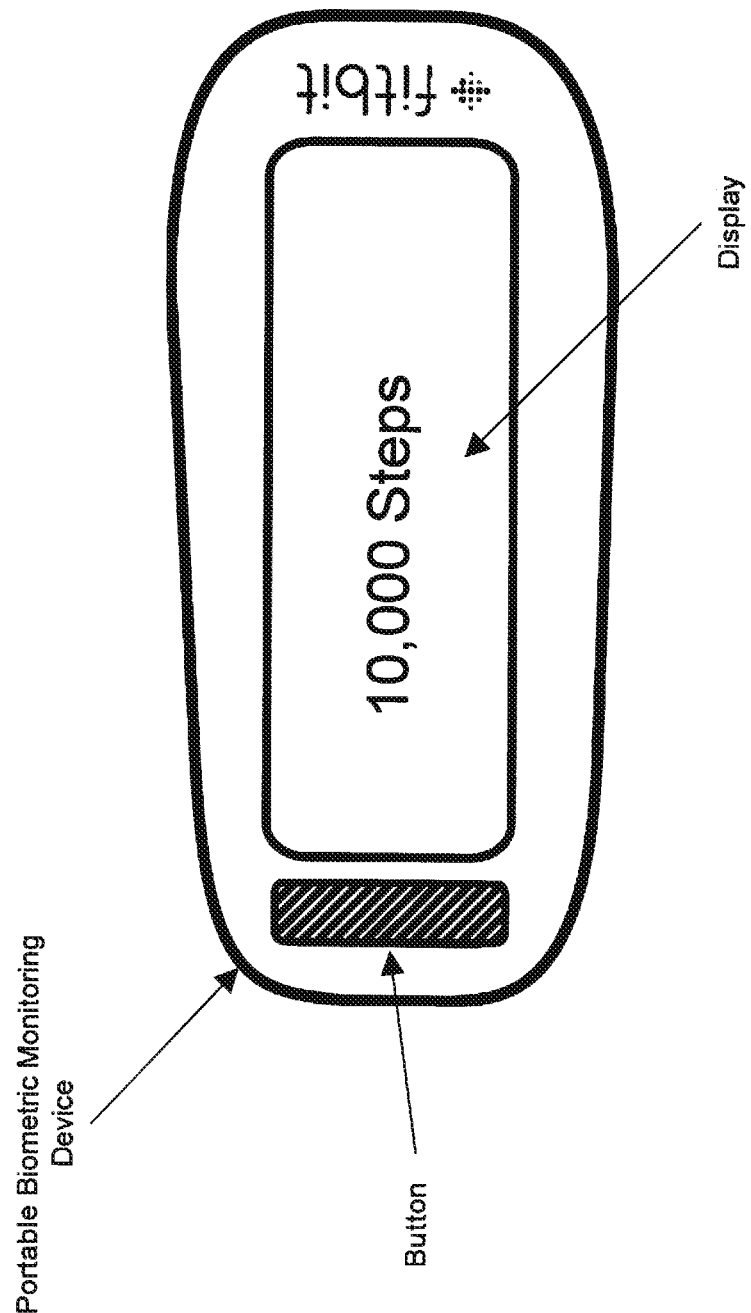

FIG. 1 illustrates an example of a portable biometric or activity sensor or monitoring device (hereinafter collectively "portable biometric monitoring device") having a button and a display and including a housing having a physical size and shape that is adapted to couple to the body of the user.

Figure 2:
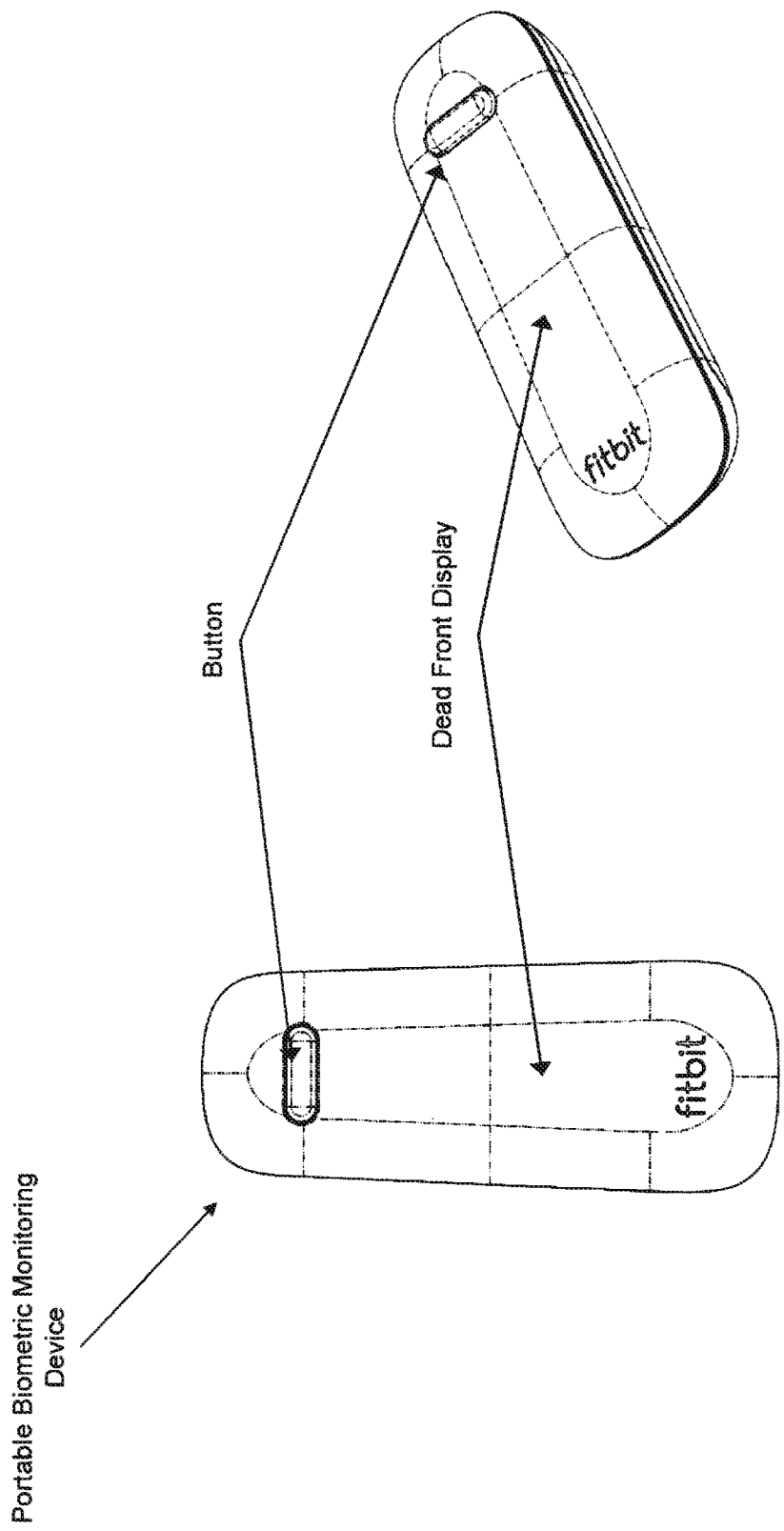

FIG. 2 illustrates an example of a portable biometric monitoring device having a button and a dead front display; notably, in the dead front display, the display is obscured from view when the display is off typically by placing a semi-transparent material in front of the display.

Figure 3:
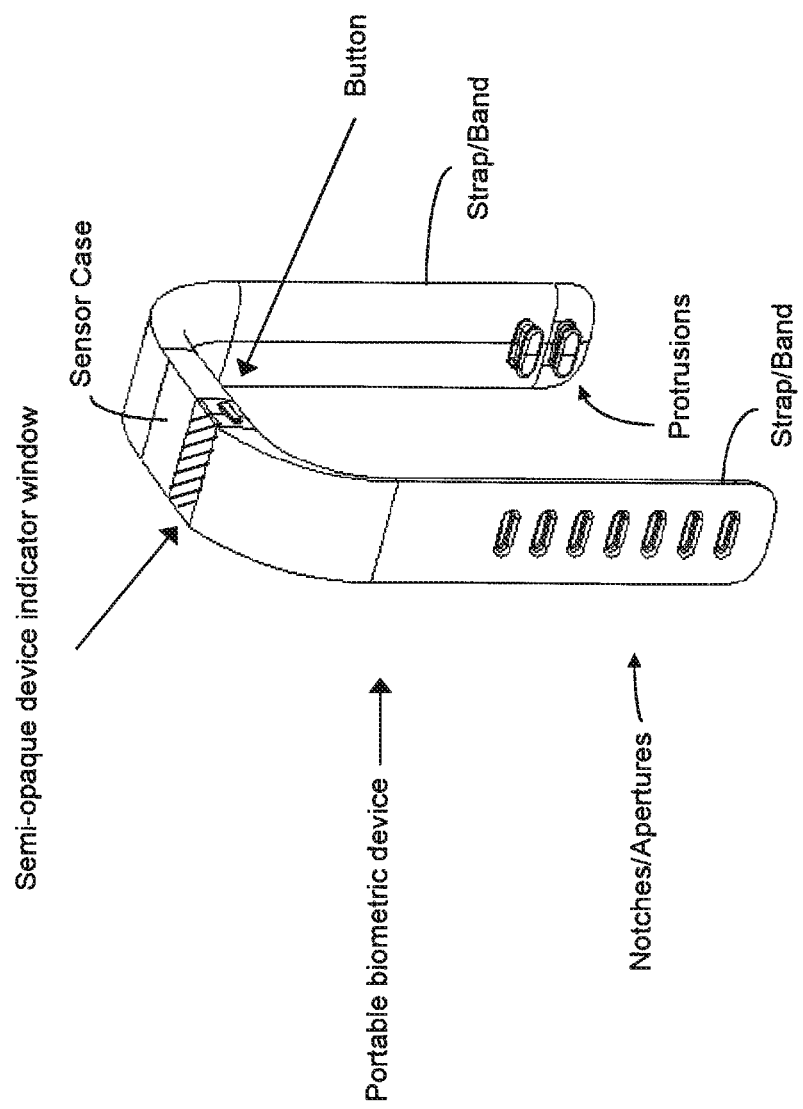

FIG. 3 illustrates a user extremity (for example, wrist or ankle) mounted portable biometric monitoring device having a button, display, and a band (having protrusions and notches/apertures) to secure the portable biometric monitoring device to the wrist or ankle of a user; notably, any mechanism or technique now known or later developed may be employed to physically couple the portable biometric monitoring device to the user.

Figure 4:
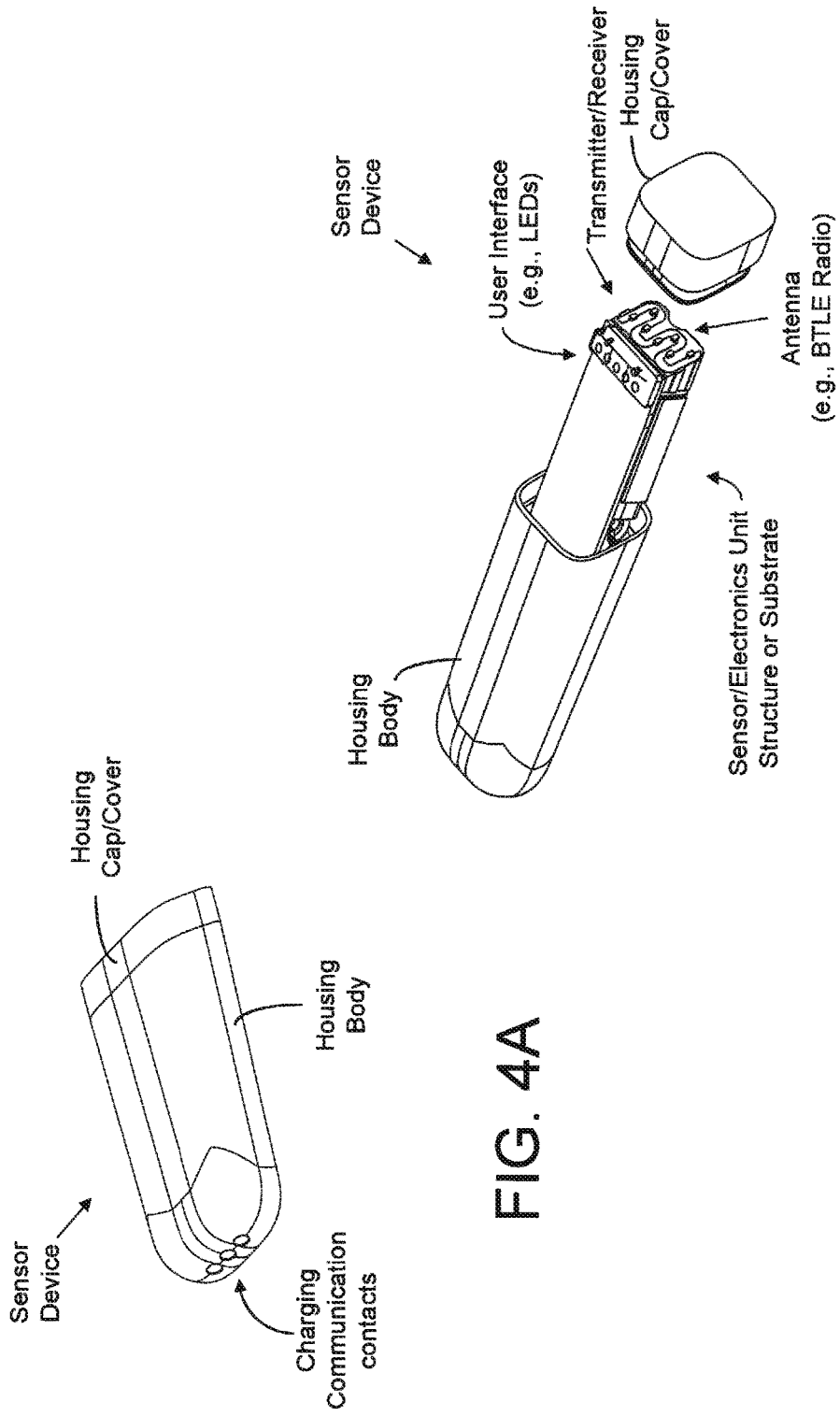

FIGS. 4A and 4B illustrates a portable biometric monitoring device having multiple LED's to display information to the user; notably, any mechanism or technique now known or later developed may be employed to physically couple or "attach" the portable biometric monitoring device to the user; for example, the sensor case of FIG. 5 may be employed or the portable biometric monitoring device attached to a band (like, for example, an arm or wrist/watch band); indeed, the portable biometric monitoring device need not include any attachment mechanism and may, for example, be physically coupled or "attached" to the user via being disposed in a pocket of clothing, a sock and/or shoe/sneaker of the user.

In one embodiment, an activity monitoring device, as shown in FIG. 4B has a housing defined by a molded structure that is elongated along a dimension that extends between a first end and a second end of the molded structure. The molded structure has an interior space. The activity monitoring device further has a circuit board dimensioned to fit within the interior space. The circuit board has a sensor, an electronics unit, and a memory. The memory is used for storing activity data and the circuit board further has an antenna and at least one light emitting diode. The activity monitoring device has a cap that connects to the second end of the molded structure to enclose the circuit board within the interior space. The activity monitoring device has a communication contact disposed at a surface of the first end of the molded structure. The communication contact provides a contact to charge a battery that is coupled to the circuit board.

In an embodiment, light emitted from the at least one light emitting diode, when active, is viewable from an exterior surface of the molded structure.

In one embodiment, the antenna communicates via radio frequency waves with a computing device to facilitate communication of the activity data or receive instructions from the computing device.

In one embodiment, the molded structure has an opening at the second end to allow entry from and exit of the circuit board with respect to the interior space.

In an embodiment, the interior space is bounded by walls of the molded structure and the opening. The first end includes one of the walls.

In one embodiment, the second end encompasses an opening to allow passage of the circuit board into and out of the opening.

In an embodiment, the cap includes a lip portion that fits within the housing.

In one embodiment, activity data includes an environmental metric or a physiological metric.

In an embodiment, the activity monitoring device includes a transmitter and receiver unit associated with the circuit board and coupled to the antenna to enable communication of the activity data.

In one embodiment, the activity monitoring device includes a transmitter and receiver unit. The electronics unit sends the activity data via the transmitter unit and the antenna to a computing device.

In an embodiment, the computing device includes a portable electronic device.

In one embodiment, the cap detaches from the second end of the molded structure to allow removal of the circuit board from the interior space.

In one embodiment, the molded structure has a substantially tubular shape.

In an embodiment, the substantially tubular shape has rounded edges and substantially straight walls.

In one embodiment, the electronics unit is configured to receive the activity data from the sensor for storage in the memory or for transferring to a computing device via the antenna.

In an embodiment, a method includes generating activity data when a user is performing an activity. The activity data is detected by a sensor of a monitoring device worn by a user. The method further includes accessing the activity data from a memory device of the monitoring device. The memory device is located in an interior space of a housing of the monitoring device. The method includes communicating the activity data from an electronic device located inside the housing via a transmitter and an antenna to a computing device located outside the housing. The antenna and the transmitter are located inside the housing. The housing is enclosed by a cap and includes a battery that is charged via a communication contact. The communication contact is located at a first end of the housing and the antenna located at a second end of the housing.

In an embodiment, the method includes sending pairing information associated with the monitoring device via a computing device to a server. The method includes pairing of the monitoring device with the computing device after the pairing information is received by the computing device from the server.

In one embodiment, the method includes sending the activity data via a computing device to a server.

In an embodiment, the activity includes swimming, bicycling, or sleeping.

Figure 5:
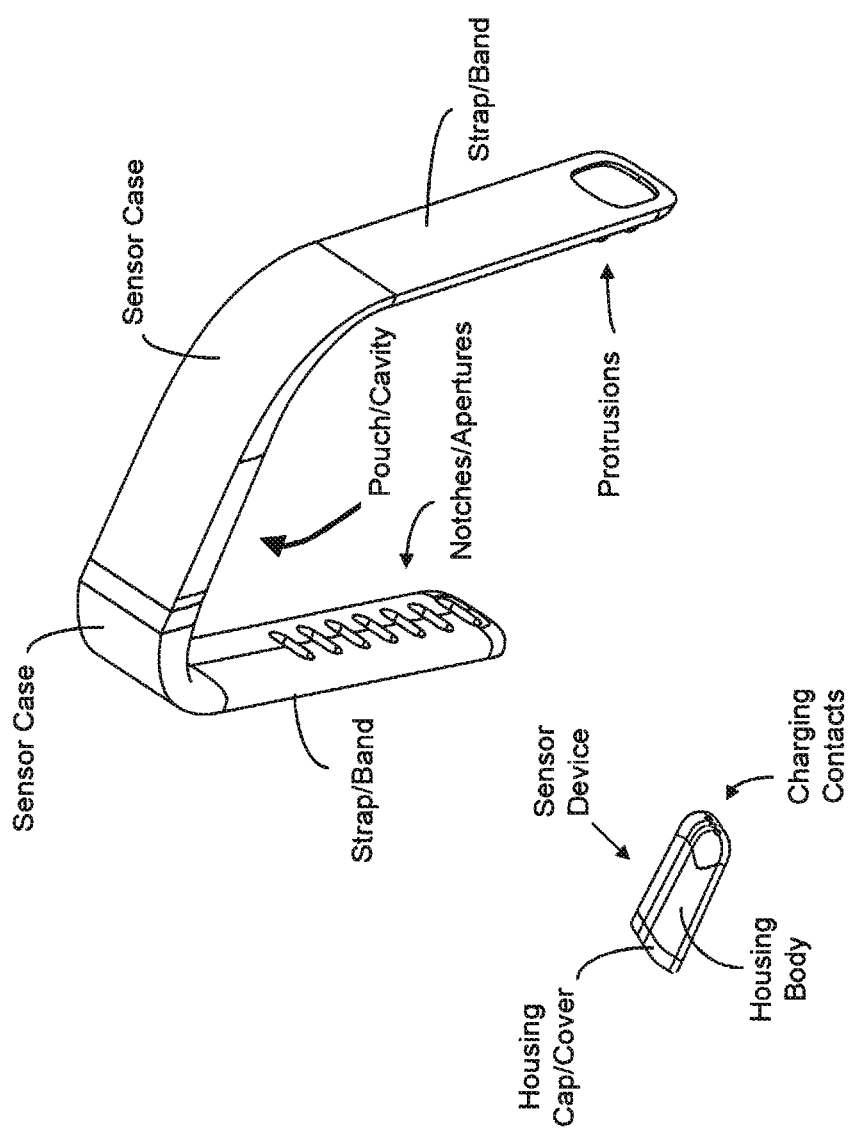
Figure 6:
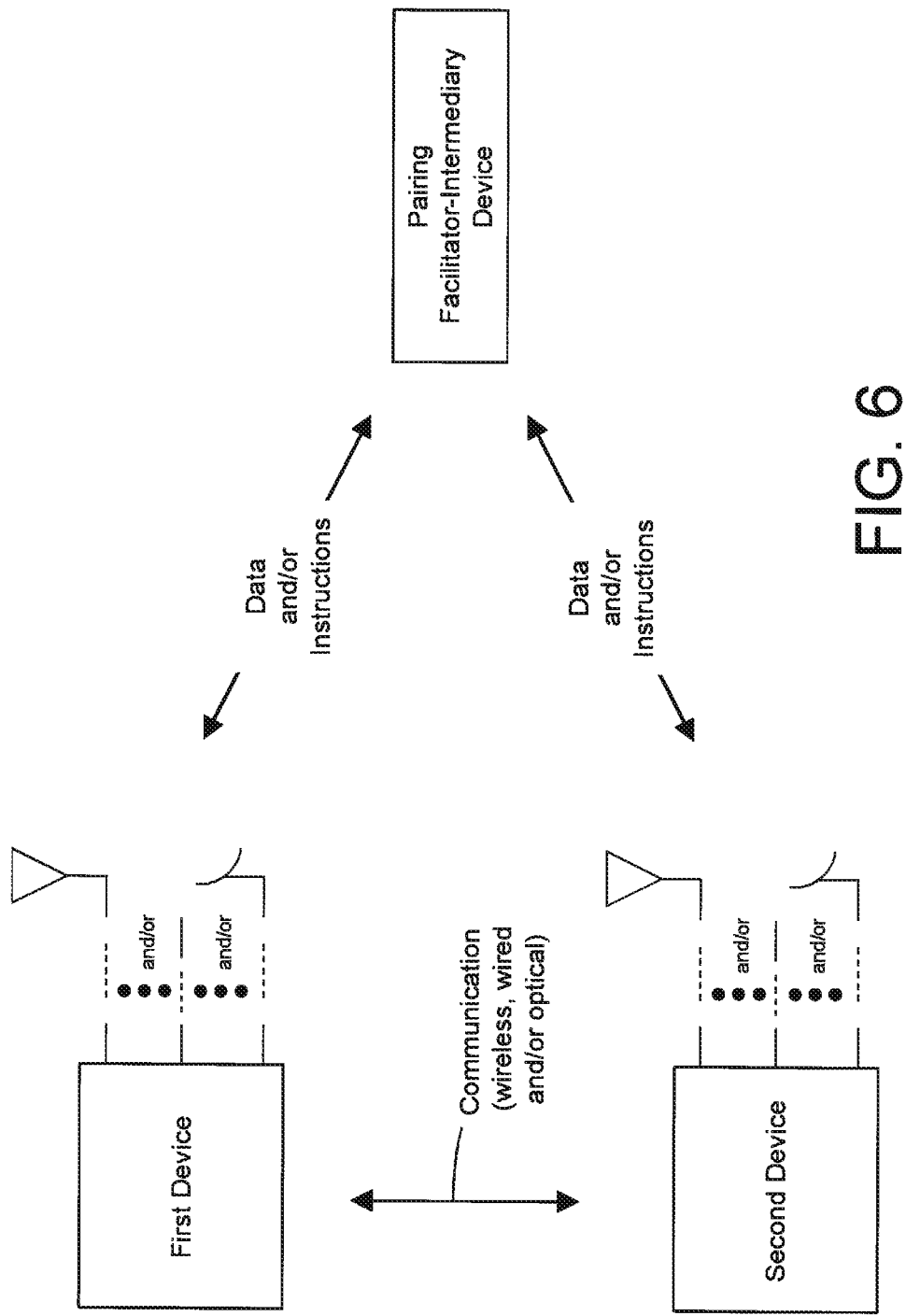
Figure 7:
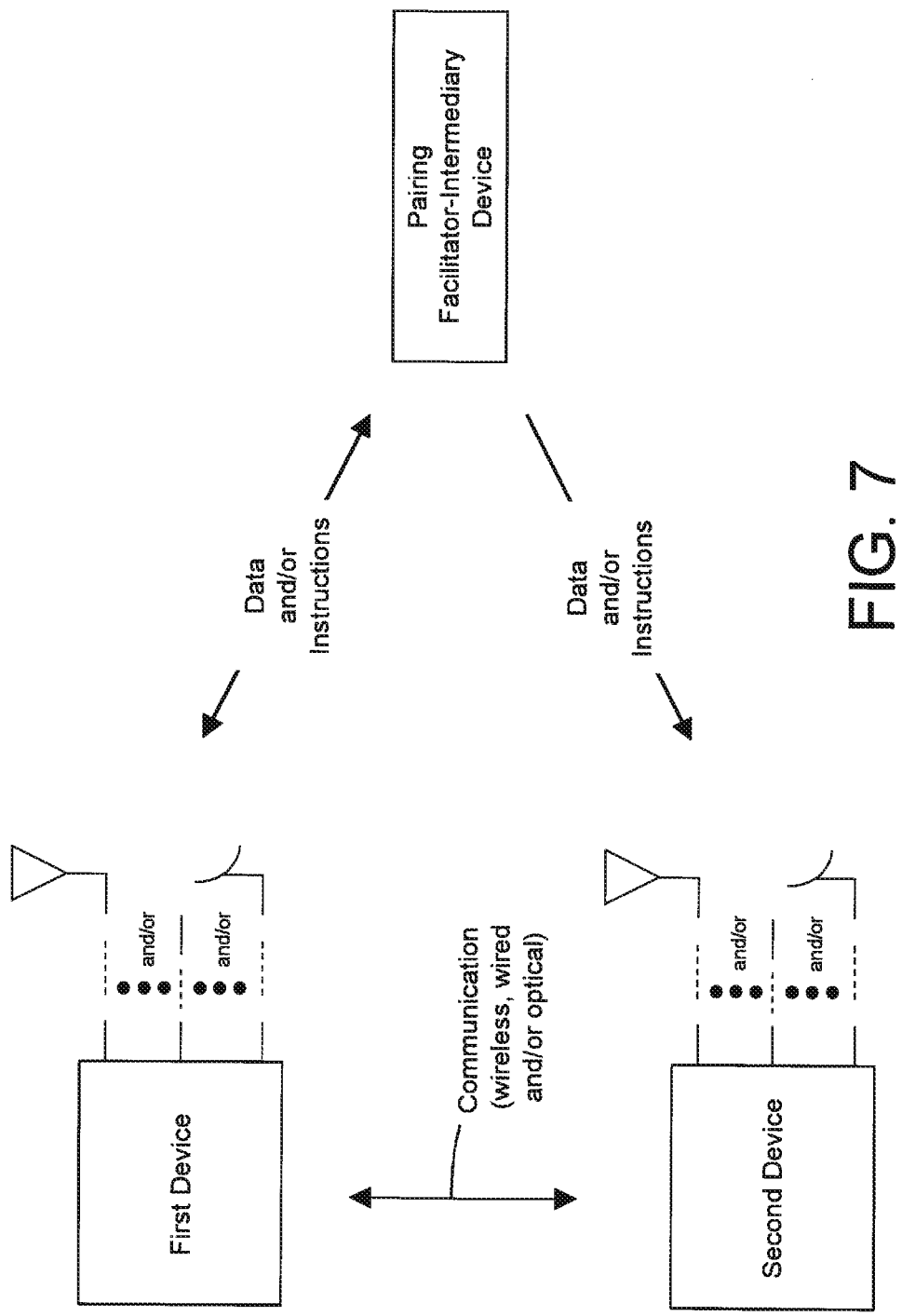

FIG. 5 illustrates a band case for a portable biometric monitoring device and a portable biometric monitoring device having multiple LED's to display information to the user, wherein this illustrative example, a sensor case (in which the portable biometric monitoring device may be disposed during operation) is physically coupled to the user via straps/bands having protrusions or posts (or the like) on the first strap/band to engage notches or apertures on the second strap/band to secure the sensor case to the user (for example, to a wrist, arm or leg); notably, any mechanism or technique now known or later developed may be employed to physically couple the sensor case and/or portable biometric monitoring device to the user—for example, the sensor case may be attached to a band (like, for example, an arm or wrist/watch band); indeed, the sensor case and/or portable biometric monitoring device need not include any attachment mechanism and may, for example, be physically coupled or "attached" to the user via being disposed in a pocket of clothing, a sock and/or shoe/sneaker of the user.

In an embodiment, a wearable band includes a strap having a protrusion located along a portion of a length of the strap. The strap has notches located along another portion of the length of the strap. The protrusion engages with a selected one of the notches. The wearable band includes a cavity for holding an activity monitoring device. The activity monitoring device includes a housing defined by a molded structure that is elongated along a dimension that extends between a first end and a second end of the molded structure. The molded structure has an interior space. The activity monitoring device further includes a circuit board dimensioned to fit within the interior space. The circuit board has a sensor, an electronics unit, and a memory. The memory stores activity data. The circuit board has an antenna and at least one light emitting diode. The activity monitoring device has a cap that connects to the second end of the molded structure to enclose the circuit board within the interior space. The activity monitoring device includes a communication contact disposed at a surface of the first end of the molded structure. The communication contact provides a contact to charge a battery that is coupled to the circuit board.

In one embodiment, the strap has a width and a depth and the length is greater than the width and the width is greater than the depth.

In an embodiment, the protrusion extends into and fit with one of the notches.

In an embodiment, one of the notches includes an aperture for surrounding the protrusion when engaged with the protrusion.

In an embodiment, the activity monitoring device includes at one light emitter. Light emitted from the at least one light emitter, when active, is viewable from an exterior surface of the molded structure.

In one embodiment, a method includes generating activity data when a user is performing an activity. The activity data is detected by a sensor of a monitoring device that fits within a pouch of a strap. The strap has a protrusion located along a portion of a length of the strap. The strap has notches located along another portion of the length of the strap. The protrusion engages with a selected one of the notches. The method further includes accessing the activity data from a memory device of the monitoring device. The memory device is located in an interior space of a housing of the monitoring device. The method includes communicating the activity data from an electronic device located inside the housing via an antenna to a computing device located outside the housing. The antenna is located inside the housing, which is enclosed by a cap. The housing includes a battery for being charged via a communication contact, which is located at a first end of the housing. The antenna is located at a second end of the housing.

In an embodiment, the method includes sending pairing information associated with the monitoring device via a computing device to a server. The method further includes pairing with the computing device after the pairing information is received by the computing device from the server.

FIGS. 6-9 illustrate, in block diagram form, embodiments having a first device (for example, a portable biometric monitoring device), second device (for example, a smartphone) and facilitator-intermediary device (for example, a server) wherein interaction between the first device and second device with a pairing facilitator-intermediary device facilitate pairing or registering processes, according to embodiments of the present inventions; in one embodiment, the first and second device directly communicate with each other as well as communicate (for example, send and/or receive data and/or instructions) with the pairing facilitator-intermediary device to enable and/or implement the pairing or registering process (see, for example, FIG. 6); in another embodiment, the first device bi-directionally communicates (for example, sends and/or receives data and/or instructions) with the pairing facilitator-intermediary device, the second device receives data and/or instructions from the pairing facilitator-intermediary device, and the first and second devices communicate to implement the pairing or registering process (see, for example, FIG. 7); in another embodiment, the first device communicates (for example, sends and/or receives data and/or instructions) with the pairing facilitator-intermediary device and the second device sends data to the pairing facilitator-intermediary device, wherein the first and second devices communicate to implement the pairing or registering process (see, for example, FIG. 8); in yet another embodiment, the first device communicates (for example, sends and/or receives data and/or instructions with the pairing facilitator-intermediary device) and the first and second devices communicate to implement the pairing or registering process (see, for example, FIG. 9); notably, the first and second devices may communicate using any technique, protocols and/or circuitry now known or later developed including wireless, wired and optical techniques; moreover, it should be noted that the communication channel between first and second device may be unsecure before pairing is complete whereas the communication channel between the first device and the pairing facilitator-intermediary device (and, in certain embodiments, to the secondary device as well) and/or the communication channel between the second device and the pairing facilitator-intermediary device (and, in certain embodiments, to the first device as well) are trusted or secure communication channel(s) after the first and second device have been paired to the pairing facilitator-intermediary device (see, for example, FIGS. 6-14,16 and 17).

FIGS. 10-13 illustrate, in block diagram form, embodiments having a first device, second device, third device and facilitator-intermediary device wherein the interaction between the first device and second device with each other and with a pairing facilitator-intermediary device to facilitate pairing or registering processes, according to embodiments of the present inventions; in one embodiment, the first and second device may communicate directly with facilitator-intermediary device and exchange secure data and/or instructions through a third device to enable and/or implement the pairing or registering process; the notably, the embodiment of exchanging secure data and/or instructions through a third device to enable and/or implement the pairing or registering process may be implemented in any of the embodiments hereof, including those of FIGS. 6-9.

FIG. 14 illustrates, in block diagram form, an embodiment having a first device, second device and facilitator-intermediary device wherein the interaction between the first device and second device with a pairing facilitator-intermediary device facilitate pairing or registering processes, according to embodiments of the present inventions, wherein first and second device send and/or receive data, instructions, and/or secure data with the pairing facilitator-intermediary device through one or multiple communication channels.

FIG. 15A illustrates, in block diagram form, a first and/or second device(s) to be paired (for example, a portable biometric monitoring device, laptop, smartphone, desktop computer or server); notably, the device may communicate (for example, data and/or instructions) using any technique, protocols and/or circuitry now known or later developed including wireless, wired and optical techniques.

FIG. 15B illustrates, in block diagram form, a first and/or second device(s) having a device to be paired and an interface device, according to embodiments of the present inventions, wherein the device of FIG. 15B may be implemented in any of the embodiments described and/or illustrated herein, wherein the device to be paired (for example, a portable biometric monitoring device) and/or interface device (for example, a laptop, tablet computer, or smartphone) may send and/or receive data, for example, wirelessly; notably, the device to be paired and/or interface device may communicate with each other through one or multiple techniques, protocols and/or circuitry now known or later developed, including but not limited to wired, wireless, or optical communication.

FIG. 15C illustrates, in block diagram form, first and second devices (i.e., the devices to be paired), according to embodiments of the present inventions, second device uses circuitry in the first device to communicate (for example, send and/or receive data and/or instructions with the pairing facilitator-intermediary device) and, using the data and/or instructions, the first and second devices subsequently communicate to implement the pairing or registering process; notably, the first and second devices may communicate using any technique, protocols and/or circuitry now known or later developed including wireless, wired and optical techniques; moreover, it should be noted that the second device may communicate through a secure communication channel to the pairing facilitator-intermediary device using communication circuitry on the first device to transfer communication from the second device to the pairing facilitator-intermediary device and/or transfer communication from the pairing facilitator-intermediary device to the second device before and/or after pairing using techniques such as encryption, obfuscation, or any other method which makes it impossible or difficult for the first device to intercept, interpret, and/or modify data or instructions sent from the second device to the pairing facilitator-intermediary device and/or data or instructions sent from the pairing facilitator-intermediary device to the second device.

FIG. 16 illustrates, in block diagram form, an embodiment where a first device is already paired to a second device, but is to be paired to a third device, accordingly to an embodiment of the present inventions; here, a pairing facilitator-intermediary device may send and/or receive data and/or instructions from the second and the third device may assist or facilitate and/or automatically implement the pairing process between the first and third device.

FIG. 17 illustrates an embodiment where multiple pairing facilitator-intermediary devices in communication with each other may send and/or receive data and/or instructions with a first and/or second device, according to one or more embodiments of the presented inventions.

Again, there are many inventions described and illustrated herein. The present inventions are neither limited to any single aspect nor embodiment thereof, nor to any combinations and/or permutations of such aspects and/or embodiments. Each of the aspects of the present inventions, and/or embodiments thereof, may be employed alone or in combination with one or more of the other aspects of the present inventions and/or embodiments thereof. For the sake of brevity, many of those combinations and permutations are not discussed separately herein.

Moreover, many other aspects, inventions and embodiments, which may be different from and/or similar to, the aspects, inventions and embodiments illustrated in the drawings, will be apparent from the description, illustrations and claims, which follow. In addition, although various features and attributes have been illustrated in the drawings and/or are apparent in light thereof, it should be understood that such features and attributes, and advantages thereof, are not required whether in one, some or all of the embodiments of the present inventions and, indeed, need not be present in any of the embodiments of the present inventions.

At the outset, it should be noted that there are many inventions described and illustrated herein. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

Further, in the course of describing and illustrating the present inventions, various circuitry, architectures, structures, components, functions and/or elements, as well as combinations and/or permutations thereof, are set forth. It should be understood that circuitry, architectures, structures, components, functions and/or elements other than those specifically described and illustrated, are contemplated and are within the scope of the present inventions, as well as combinations and/or permutations thereof.

With that in mind, in one aspect, the present inventions are directed to techniques and systems having one or more pairing facilitator-intermediary devices to enable or facilitate pairing and/or registering two or more devices to, for example, recognize, interact and/or identify such devices and/or enable interoperability between such devices. In one embodiment, the pairing facilitator-intermediary device (for example, a server, laptop or desktop computer) responsively communicates data and/or instructions to one or both of the devices which, in response, enable or facilitate the two devices to pair or register. The present inventions may be advantageous where one or both of the devices to be paired or registered do not include or employ functionality and/or resident circuitry (for example, an interface (for example, a user interface) or resident communication circuitry) that allows, enables or permits a user to pair and/or register the one or more devices. For example, where the device to be paired or registered does not possess a, or employ its user interface and/or communication circuitry which is suitable for selection, entering and/or communicating data to its counterpart device (for example, via communicating out-of-band data) which would implement a pairing or registering operation. Such devices may include, but are not limited to portable biometric monitoring devices such as those shown in FIGS. 1-5 which have one or no buttons or the like (other user input mechanism).

With reference to FIGS. 6-14, one or more devices to be paired, identified or registered separately (in the illustrative example, first and second devices) communicate with a pairing facilitator-intermediary device (for example, a computer, computing system, website and/or service (and/or website or service computing host)). The first and second devices to be paired, identified or registered may communicate with the pairing facilitator-intermediary device directly and/or via an interface device (for example, any type of computing or communication device (such as a smart phone, router, and/or computer)). (See, FIGS. 15A and 15B, respectively). The communication with the interface device and the pairing facilitator-intermediary device may be, for example, wired, wireless and/or optical wherein the pairing facilitator-intermediary device provides data and/or instructions to one or both of the first and/or second devices to facilitate or enable the first and second devices to pair, register and/or identify with the other.

In one embodiment, the devices to be paired or registered (for example, automatically and/or in response to a user input) are paired or registered (for example, via the user) with the pairing facilitator-intermediary device. The pairing facilitator-intermediary device may present or offer a user or a system with one or more devices that, for example, are (i)

capable of being paired/registered, (ii) available to be paired/registered, (iii) should be paired/registered and/or (iv) currently paired/registered. In response thereto, the user or system may indicate, select and/or identify the devices to be paired/registered with each other. That is, with reference to FIG. 6, the user may indicate that the first and second devices are to be paired or registered to, for example, enable the devices to recognize, interact and/or identify each other and/or enable interoperability there between.

In response to such user or system input, the pairing facilitator-intermediary device provides information (for example, data and/or instructions) to the first and second devices that facilitate or allow such pairing or registering. Here, the pairing facilitator-intermediary may employ an existing secure connection to the first and second devices to provide information of the requested pairing/registering to one or both of the first and second devices. Note that communication between the first device and the pairing facilitator-intermediary device, between the second device and the pairing facilitator-intermediary device and between the first and second device via the pairing facilitator-intermediary device may be secure due to the completion of pairing between the first device and the pairing facilitator and the completion of pairing between the second device and the pairing facilitator. The direct communication between the first and second device may not be considered secure before the first and second devices are paired. The information of the requested pairing/registering may be suitable for the devices to perform a pairing/registering operation with each other. For example, the information may include an identifier for the intended pairing/registering partner, and a secret code, key or data that may be used or communicated as out-of-band-data (for example, via short-range communication—such as a short-range wireless technique) between the first and second device. Notably, out-of-band-data is data which is communicated or transmitted via out-of-band-communication, which may be characterized as communication through a second communication method or channel. Note that out-of-band-data may be data which is communicated though the same electromagnetic frequency band (in the specific case of typical wireless communication) using different methods or protocols than the first "in-band" communication (for example, the communication technique and/or protocol employed by the first and/or second device in conjunction with the facilitator-intermediary device).

The first and second devices, after receipt of the information from the pairing facilitator-intermediary device, may automatically pair, register and/or recognize with each other, for example, via use of the out-of-band secret to authenticate the pairing attempt. Thereafter, the first and second devices are paired or registered to, for example, enable interoperability there between.

Notably, in one embodiment, the first and second devices may employ any communication technique and/or protocol now known or later developed including, for example, short-range (for example, less than 20 feet, and preferably less than 10 feet, and more preferably, less than 5 feet) wireless techniques including, for example, NFC, RFID or Bluetooth protocols and/or techniques. In one embodiment, such short-range communication techniques facilitate private, secret data exchange.

In another embodiment, the present inventions may be implemented where only one of the first and second devices (i.e., the devices to be paired or registered such as a portable biometric monitoring device and a portable computing device (for example, smartphone)) communicates with the pairing facilitator-intermediary device. (See, FIG. 7). In this embodiment, the pairing facilitator-intermediary device provides pairing or registering information (for example, data and/or instructions) to both devices to facilitate or allow pairing or registering. Thereafter, the first and second devices may complete the pairing operation as described above in connection with FIG. 6.

Figure 8:
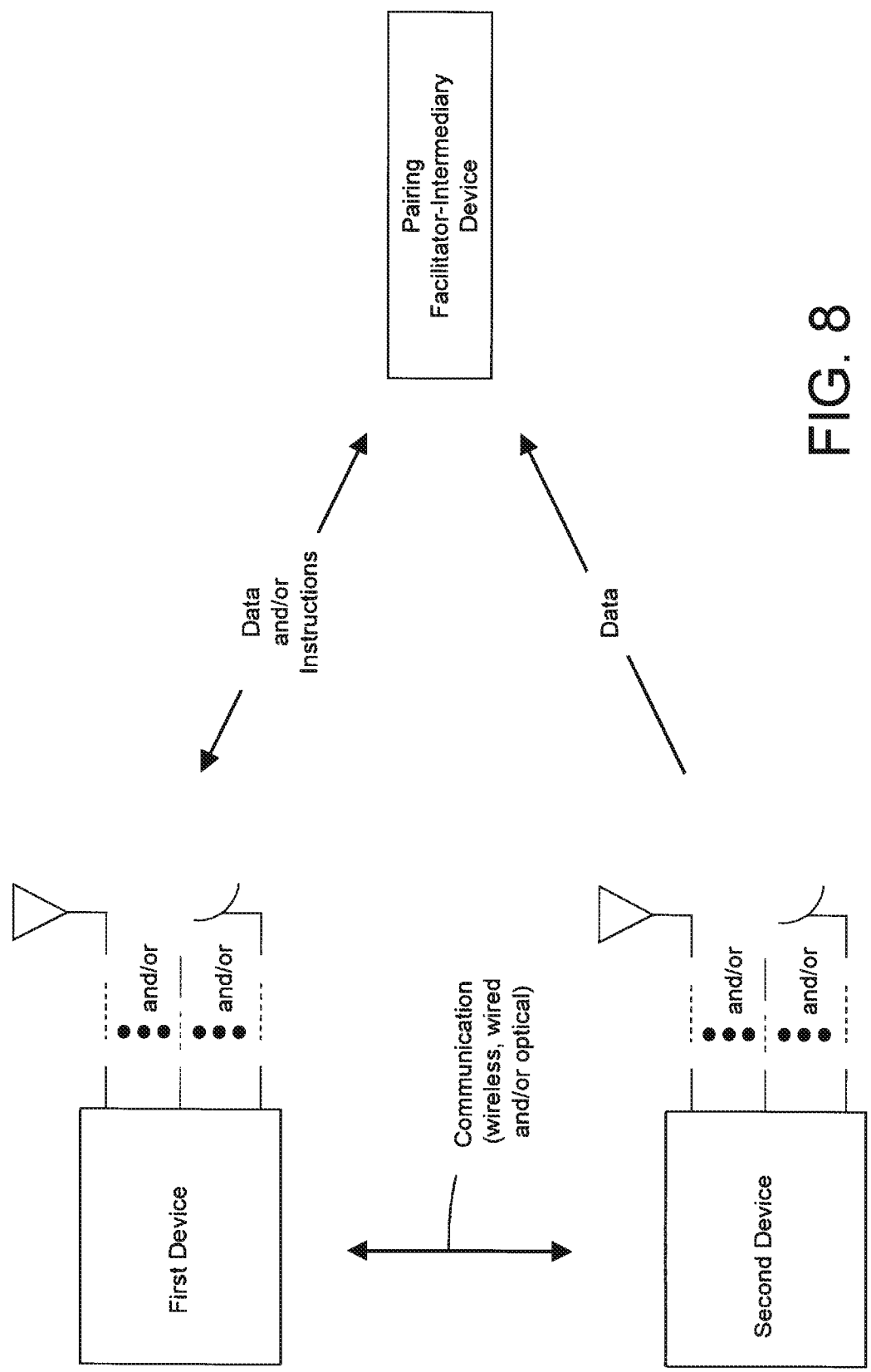
Figure 9:
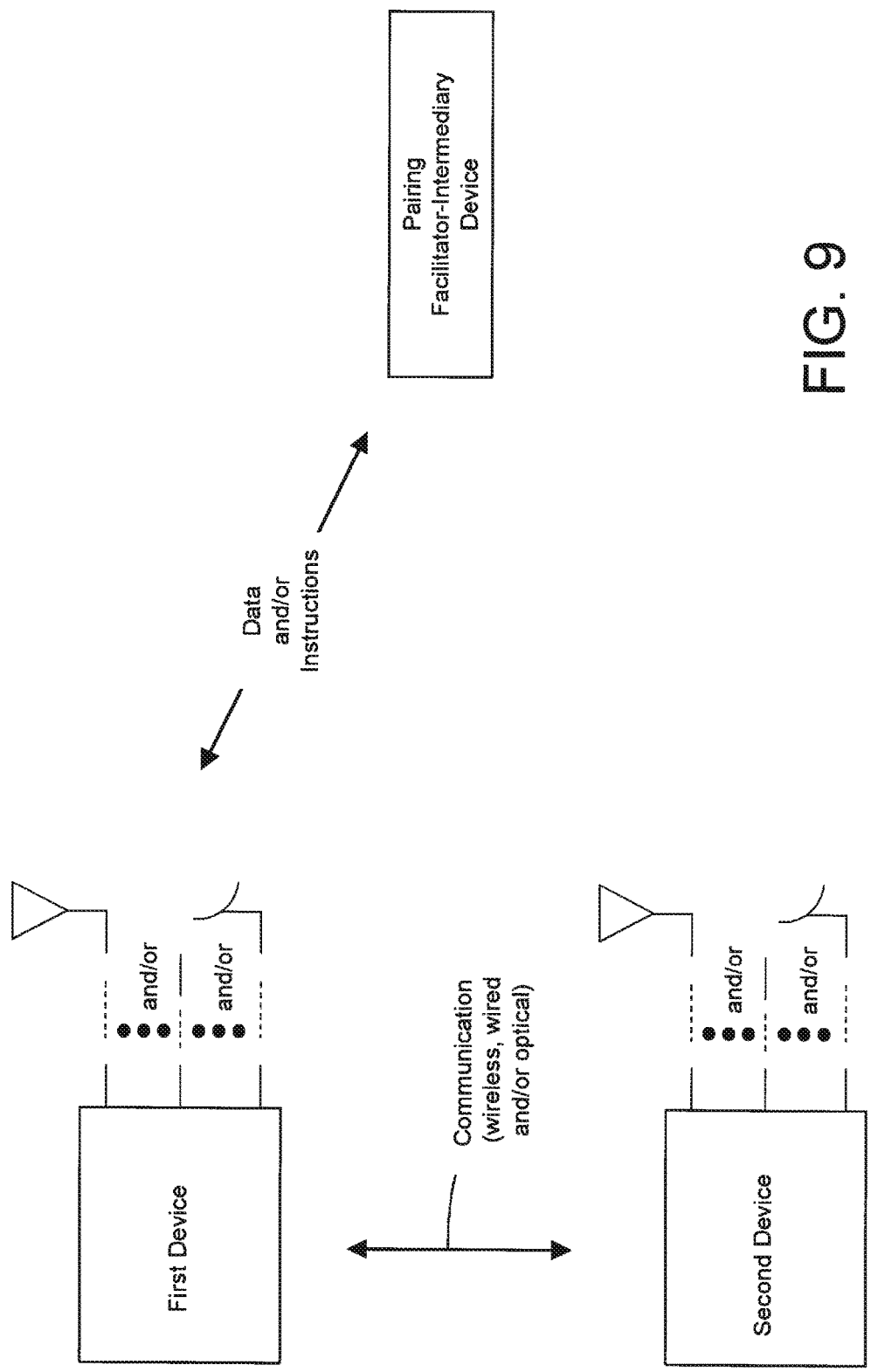
Figure 10:
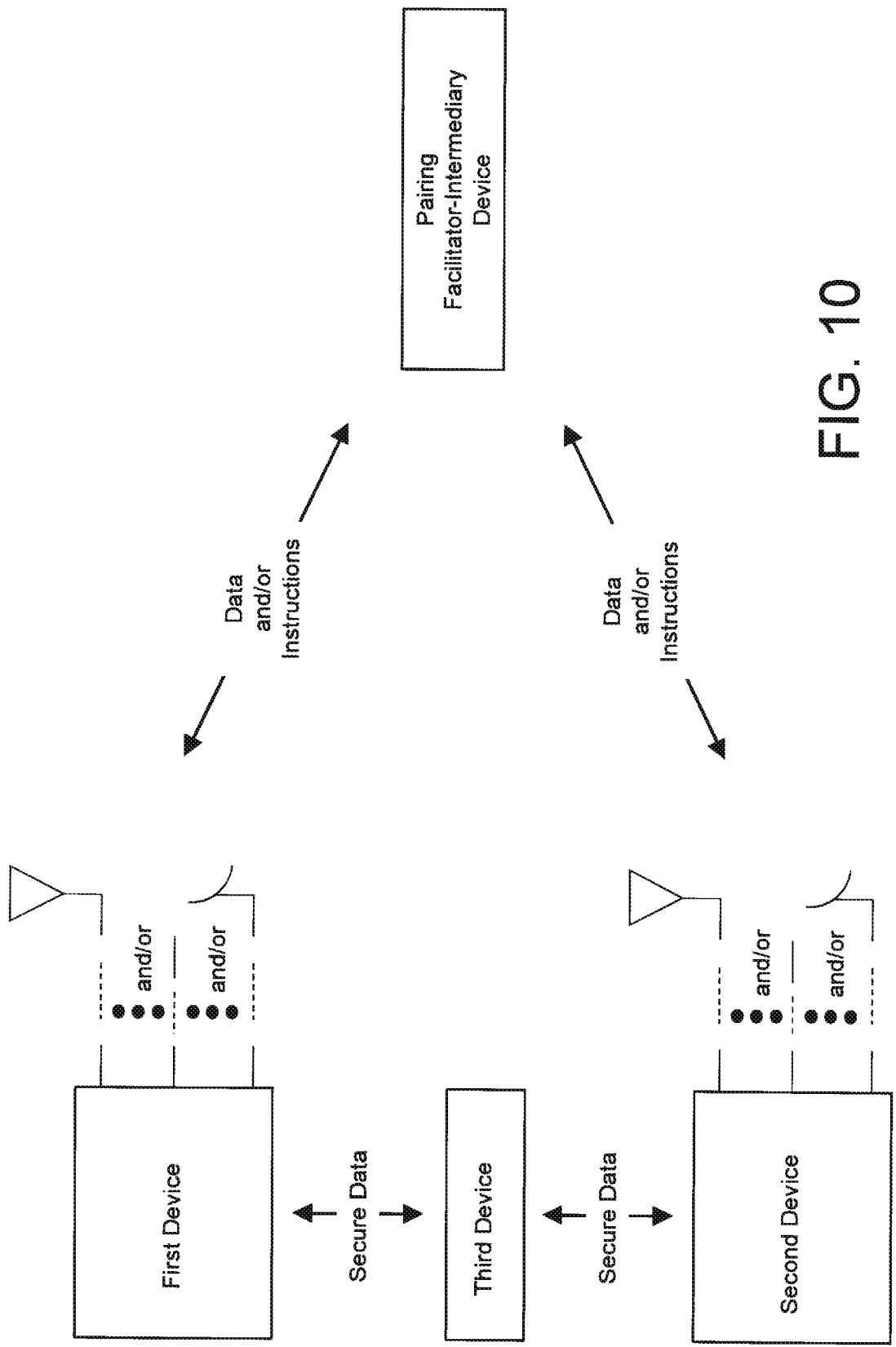

With reference to FIG. 8, in another embodiment, both the first and second devices provide data to the pairing facilitator-intermediary device—however, the pairing facilitator-intermediary device provides pairing or registering information (for example, data and/or instructions) to only one of the first and second devices. In this embodiment, the first and second devices employ such information to pair or register, for example, via the techniques described above. That is, the pairing facilitator-intermediary employs an existing secure connection to the first device to provide such pairing or registering information. The first device may use such information to perform a pairing/registering operation with the second device. For example, the pairing or registering information may include an identifier for the intended pairing/registering partner, and a secret that may be used or communicated as out-of-band-data (for example, via short-range communication—such as a short-range wireless technique). The first device, after receipt of such information from the pairing facilitator-intermediary device, may automatically initiate the pairing or registering operation with the second device, for example, via use of the out-of-band secret to authenticate the pairing attempt. Thereafter, the first and second devices are paired or registered to, for example, enable interoperability there between.

Indeed, in another embodiment, only one of the first and second devices includes any communication with the pairing facilitator-intermediary device. (See, FIG. 9). In this embodiment, the pairing facilitator-intermediary device (such as a web service hosted on an internet connected server) may provide pairing or registering information to the first device (for example, a portable computing device, laptop and/or smartphone) to allow or enable pairing/registering operation with the second device (for example, a portable biometric monitoring device or other device having limited user interface and connectivity). The pairing facilitator-intermediary device may again employ the existing secure connection to the first device to provide such information. In response, the first device may initiate pairing/registering and use the information to perform a pairing/registering operation with the second device. Here again, the information may include an identifier for the intended pairing/registering partner, and a secret (for example, a secret code, key or instruction (which may initiate or implement a certain operation such as, for example, generation of a code) that may be used or communicated as out-of-band-data (for example, via short-range communication—such as a short-range wireless technique). Thereafter, the first and second devices may "complete" the pairing operation as described above.

There are many inventions described and illustrated herein. While certain embodiments, features, attributes and advantages of the inventions have been described and illustrated, it should be understood that many others, as well as different and/or similar embodiments, features, attributes and advantages of the present inventions, are apparent from the description and illustrations. As such, the embodiments, features, attributes and advantages of the inventions described and illustrated herein are not exhaustive and it should be understood that such other, similar, as well as different, embodiments, features, attributes and advantages of the present inventions are within the scope of the present inventions.

For example, although the embodiments described herein employ first and second devices communicating directly after receipt of the pairing or registering information from the pairing facilitator-intermediary device, such communication may be via a third device and/or via the pairing facilitator-intermediary device. As such, in this exemplary embodiment, not only is the communication between the first and second devices indirect—the actual pairing/registering function or interaction may be indirect, for example, via the third device. (See, for example, FIGS. 7-14).

In addition, as noted above, the first and second devices to be paired, identified or registered may communicate with the pairing facilitator-intermediary device directly and/or via an interface device. (See, FIGS. 15A and 15B, respectively). Here, communication between the first and second devices to be paired, identified or registered and the pairing facilitator-intermediary device is enabled or provided through, for example, client programs, which operate or run on the interface device (for example, the computing or communication device (such as a smart phone, router, and/or computer)).

Notably, the present inventions may be advantageous where one or both of the devices to be paired or registered do not include or employ the functionality and/or circuitry that enables or permits pairing and/or registering of the devices. For example, where the device to be paired or registered does not possess a, or employ its user interface and/or communication circuitry which is suitable for selection, entering and/or passing out-of-band data.

In the case where it is desirable to pair a single first device to one or more other devices, (for example, a second and third device as seen in FIG. 16), a pairing facilitator may send and/or receive data and/or instructions from a second device which is already paired to the first device to a pairing facilitator-intermediary device. The pairing facilitator-intermediary device may also send and/or receive data and/or instructions with the third device to facilitate the pairing of the first device to the third device. Notably, the embodiment of FIG. 16 may be employed in connection with other embodiments described and/or illustrated herein (for example, FIGS. 6-14).

It should also be noted that in some embodiments of the present inventions, the pairing facilitator-intermediary device may consist of a chain or network of one or more pairing facilitator-intermediary devices in communication with each other (see FIG. 17). That is, although the pairing facilitator-intermediary device is primarily described and illustrated as one device—the pairing facilitator-intermediary device may include a plurality of interconnected devices—for example, the embodiments of FIGS. 6-14 may be implemented using or with a plurality of pairing facilitator-intermediary devices. For the sake of brevity, those embodiments will not be repeated with a plurality of pairing facilitator-intermediary devices.

Further, in one embodiment, the second device (for example, a portable biometric monitoring device) may employ circuitry in the first device (for example, a smartphone, laptop and/or tablet) to communicate (for example, send and/or receive data and/or instructions) with the pairing facilitator-intermediary device. (See, FIG. 15C). Here, the pairing facilitator-intermediary device may send the information (for example, data and/or instructions (for example, a secret code, data or key)) to the second device via the first device and, using that information (for example, data and/or instructions), the first and second devices may subsequently communicate to implement the pairing or registering process. Thus, the first device (which function or operates as an interface device for the second device) allows, enables or permits the second device to communicate (and, in one embodiment, pair) to the pairing facilitator-intermediary device to subsequently pair and/or register the first and second devices. Note that the second device may communicate through a secure communication channel to the pairing facilitator-intermediary device using communication circuitry on the first device to transfer communication from the second device to the pairing facilitator-intermediary device and/or transfer communication from the pairing facilitator-intermediary device to the second device before and/or after pairing using techniques such as encryption, obfuscation, or any other method which makes it impossible or difficult for the first device to intercept, interpret, and/or modify data or instructions sent from the second device to the pairing facilitator-intermediary device and/or data or instructions sent from the pairing facilitator-intermediary device to the second device.

Notably, in one embodiment, the first device of FIG. 15C may be one or more of the biometric monitoring devices described and/or illustrated in U.S. patent application Ser. No. 13/346,275, entitled "Biometric Monitoring Device having Body Weight Sensor, and Methods of Operating Same", filed Jan. 9, 2012, Inventor: Yuen et al. (which is incorporated herein, in its entirety, by reference). For example, in one embodiment, a second device, for example, a portable activity monitoring device (for example, a device as or like that illustrated in FIGS. 1-5) communicates with the pairing facilitator-intermediary device via a biometric monitoring device (for example, of the type described and/or illustrated in the '275 application). That is, in one embodiment, the first and/or second devices communicate(s) (for example, pair and/or register) with the facilitator-intermediary device (for example, a server) and receive information such as data and/or instructions (for example, a secret code, data or key) which is to be used in the pairing or registering process between the first and second devices (here, a portable activity monitoring device and a biometric monitoring device having a body weight sensor). The pairing facilitator-intermediary device provides the information to the second device via the first device (for example, using communication circuitry of the first device). Notably, the pairing facilitator-intermediary device may also send information to the first device.

Using the information (for example, a secret code, data or key), the first and second devices may subsequently communicate to pair or register to enable interoperability between the first and second devices and/or an initialization process which creates a link (for example, a lasting and/or sustainable link) between two or more devices to facilitate, allow and/or make possible future communication between the devices. Indeed, after the pairing or registering process is complete, the first and/or second devices may save information about one or more of the other devices so that when a new, subsequent and/or future communication link is to be set-up, little or no user interaction is required to create the connection.

Importantly, the present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof.

Notably, the present inventions may be employed in conjunction with the inventions described and/or illustrated in U.S. patent application Ser. No. 13/785,904, which is hereby incorporated by reference. For example, after pairing of the first and second devices using any of the embodiments described and/or illustrated herein, such first and second devices may communicate using the circuitry, architectures and/or techniques described and/or illustrated in U.S. patent application Ser. No. 13/785,904 (Entitled "Near Field Communication System, and Method of Operating Same", Inventor: Park, Filed on Mar. 15, 2013). For the sake of brevity, such combinations will not be set forth in detail herein—except by reference.

It should be noted that the devices, circuitry, architectures and/or structures disclosed herein (circuitry of the processing device, sensor device and/or proxy device) may be described using computer aided design tools and expressed (or represented), as data and/or instructions embodied in various computer-readable media, in terms of their behavioral, register transfer, logic component, transistor, layout geometries, and/or other characteristics. Formats of files and other objects in which such structure expressions may be implemented include, but are not limited to, formats supporting behavioral languages such as C, Verilog, and HLDL, formats supporting register level description languages like RTL, and formats supporting geometry description languages such as GDSII, GDSIII, GDSIV, CIF, MEBES and any other suitable formats and languages. Computer-readable media in which such formatted data and/or instructions may be embodied include, but are not limited to, non-volatile storage media in various forms (for example, optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the Internet and/or other computer networks via one or more data transfer protocols (for example, HTTP, FTP, SMTP, etc.).

Indeed, when received within a computer system via one or more computer-readable media, such data and/or instruction-based expressions of the circuitry of the processing device, sensor device and/or proxy device within the computer system in conjunction with execution of one or more other computer programs including, without limitation, netlist generation programs, place and route programs and the like, to generate a representation or image of a physical manifestation of such structures. Such representation or image may thereafter be used in device fabrication, for example, by enabling generation of one or more masks that are used to form various components of the structures in a device fabrication process.

Moreover, the various devices, circuitry, architectures and/or structures disclosed herein may be represented via simulations using computer aided design and/or testing tools. The simulation of the circuitry of the processing device, sensor device and/or proxy device, and/or characteristics or operations thereof, may be implemented by a computer system wherein characteristics and operations of such structures, and techniques implemented thereby, are imitated, replicated and/or predicted via a computer system. The present inventions are also directed to such simulations of the inventive structures, and/or techniques implemented thereby, and, as such, are intended to fall within the scope of the present inventions. The computer-readable media corresponding to such simulations and/or testing tools are also intended to fall within the scope of the present inventions.

The term "non-pairable user interface" if/when used in the claims means, among other things, a user interface that is not configured, enabled or suitable to pair and/or register an associated device, for example, by selecting or entering data or commands to a device to which it is to be paired (for example, via communicating data or commands using an out-of-band protocol/technique (relative to communication protocol/technique in connection with the pairing to the facilitator-intermediary device).

Further, in the claims, the phrase "in response to pairing to the facilitator-intermediary device" has no express or implied immediate temporal component, implication or inference and, as such, an operation or action "in response to pairing to the facilitator-intermediary device" may be immediately after pairing or anytime thereafter.

Notably, the terms "first," "second," and the like, herein do not denote any order, quantity, or importance, but rather are used to distinguish one element from another. Moreover, in the claims, the terms "a" and "an" herein do not denote a limitation of quantity, but rather denote the presence of at least one of the referenced item.

What is claimed is:

1. A computing device, comprising:
   communication circuitry;
   a display;
   a processor coupled to the communication circuitry; and
   a memory storing computer-executable instructions which, when executed, cause the processor to:
      receive, by the communication circuitry, a list of one or more devices capable of being paired with the computing device, the list of one or more devices including a portable monitoring device, the list being received from a server via a network, the server further being in operative communication with the one or more devices pairable with the computing device via an existing secure connection;
      display, via the display, the list of one or more devices;
      receive an indication of a selection of the portable monitoring device to be paired with the computing device;
      send first pairing information to the portable monitoring device via a wireless protocol;
      receive second pairing information from the portable monitoring device via the wireless protocol; and
      pair the computing device with the portable monitoring device based on the first and second pairing information.

2. The computing device of claim 1, wherein pairing the computing device with the portable monitoring device comprises creating a link between the computing device and the portable monitoring device, the memory further comprising computer-executable instructions which, when executed, cause the processor to:
   receive, by the communication circuitry, activity data from the portable monitoring device via the link,
   wherein the activity data is representative of a physiological metric collected by one or more sensors embedded in the portable monitoring device.

3. The computing device of claim 1, wherein the first pairing information comprises an identifier of the computing device and a first secret code and wherein the second pairing information comprises an identifier of the portable monitoring device and a second secret code.

4. The computing device of claim 1, wherein the portable monitoring device lacks a user interface for receiving unencrypted pairing information.

5. The computing device of claim 1, wherein the server is paired with the computing device and each of the devices in the list of one or more devices.

6. The computing device of claim 1, wherein the computing device is configured to communicate with the potable monitoring device via a communication protocol that is different from a communication protocol used to communicate with the pairing facilitator server.

7. A non-transitory computer readable storage medium having stored thereon instructions that, when executed, cause a processor of a computing device to:
   receive, by communication circuitry of the computing device, a list of one or more devices capable of being paired with the computing device, the list of one or more devices including a portable monitoring device, the list being received from a server via a network, the server further being in operative communication with the one or more devices pairable with the computing device via an existing secure connection;
   display, via a display of the computing device, the list of one or more devices;
   receive an indication of a selection of the portable monitoring device to be paired with the computing device;
   send first pairing information to the portable monitoring device via a wireless protocol;
   receive second pairing information from the portable monitoring device via the wireless protocol; and
   cause the computing device to be paired with the portable monitoring device based on the first and second pairing information.

8. The non-transitory computer readable storage medium of claim 7, wherein causing the computing device to be paired with the portable monitoring device comprises creating a link between the computing device and the portable monitoring device, the non-transitory computer readable storage medium further having stored thereon instructions that, when executed, cause the processor to:
   receive, by the communication circuitry, activity data from the portable monitoring device via the link,
   wherein the activity data is representative of a physiological metric collected by one or more sensors embedded in the portable monitoring device.

9. The non-transitory computer readable storage medium of claim 7, wherein the first pairing information comprises an identifier of the computing device and a first secret code and wherein the second pairing information comprises an identifier of the portable monitoring device and a second secret code.

10. The non-transitory computer readable storage medium of claim 7, wherein the portable monitoring device lacks a user interface for receiving unencrypted pairing information.

11. A method for pairing a portable monitoring device with a computing device, comprising:
   receiving, by the computing device, a list of one or more devices capable of being paired with the computing device, the list of one or more devices including the portable monitoring device, the list being received from a server via a network, the server further being in operative communication with the one or more devices pairable with the computing device via an existing secure connection;
   displaying, via a display of the computing device, the list of one or more devices;
   receiving an indication of a selection of the portable monitoring device for pairing with the computing device;
   sending first pairing information to the portable monitoring device via a wireless protocol;
   receiving second pairing information from the portable monitoring device via the wireless protocol; and
   causing the computing device to be paired with the portable monitoring device based on the first and second pairing information.

12. The method of claim 11, wherein causing the computing device to be paired with the portable monitoring device comprises creating a link between the computing device and the portable monitoring device, the method further comprising:
   receiving, by the computing device, activity data from the portable monitoring device via the link,
   wherein the activity data is representative of a physiological metric collected by one or more sensors embedded in the portable monitoring device.

13. The method of claim 11, wherein the first pairing information comprises an identifier of the computing device and a first secret code and wherein the second pairing information comprises an identifier of the portable monitoring device and a second secret code.

14. The method of claim 11, wherein the portable monitoring device lacks a user interface for receiving unencrypted pairing information.

15. The method of claim 11, wherein the server is paired with the computing device and each of the devices in the list of one or more devices.

16. The method of claim 11, wherein the computing device is configured to communicate with the potable monitoring device via a communication protocol that is different from a communication protocol used to communicate with the pairing facilitator server.

17. The method of claim 11, wherein the portable monitoring device includes a sensor for sensing physiological metrics of a user while the portable monitoring device is worn by the user, and wherein the portable biometric device includes a housing that houses the sensor and has a dead front display and a button.

* * * * *